US011369697B2

(12) United States Patent
Kamaly et al.

(10) Patent No.: US 11,369,697 B2
(45) Date of Patent: Jun. 28, 2022

(54) LIPOSOME NANOPARTICLES FOR TUMOR MAGNETIC RESONANCE IMAGING

(71) Applicants: UNITED KINGDOM RESEARCH AND INNOVATION, Swindon (GB); Imperial Innovations Limited, South Kensington (GB)

(72) Inventors: Nazila Kamaly, London (GB); Tammy Louise Kalber, London (GB); Gavin David Kenny, London (GB); Maya Thanou, London (GB); Andrew David Miller, London (GB); Jimmy David Bell, London (GB)

(73) Assignees: UNITED KINGDOM RESEARCH AND INNOVATION, Swindon (GB); IMPERIAL INNOVATIONS LIMITED, London (GB)

( * ) Notice: Subject to any disclaimer, the term of this patent is extended or adjusted under 35 U.S.C. 154(b) by 0 days.

(21) Appl. No.: 15/463,964

(22) Filed: Mar. 20, 2017

(65) Prior Publication Data

US 2017/0348440 A1 Dec. 7, 2017

Related U.S. Application Data

(63) Continuation of application No. 13/511,126, filed as application No. PCT/GB2010/051925 on Nov. 19, 2010, now abandoned.

(30) Foreign Application Priority Data

Nov. 20, 2009 (GB) .................................... 0920304

(51) Int. Cl.
*A61K 49/18* (2006.01)
*B82Y 5/00* (2011.01)

(52) U.S. Cl.
CPC ............ *A61K 49/1812* (2013.01); *B82Y 5/00* (2013.01); *Y10S 977/773* (2013.01)

(58) Field of Classification Search
None
See application file for complete search history.

(56) References Cited

U.S. PATENT DOCUMENTS

| | | | |
|---|---|---|---|
| 4,766,046 | A | 8/1988 | Abra et al. |
| 7,749,485 | B2 | 7/2010 | Tournier et al. |
| 2007/0286898 | A1 | 12/2007 | Takagi et al. |
| 2007/0292494 | A1 | 12/2007 | Gieseler et al. |

FOREIGN PATENT DOCUMENTS

| | | | |
|---|---|---|---|
| JP | 2006063009 | A | 3/2006 |
| JP | 2008501667 | A | 1/2008 |
| WO | WO-2005016141 | A1 | 2/2005 |
| WO | WO-2006025411 | A1 | 3/2006 |

OTHER PUBLICATIONS

Alhaique et al. Solvent 1H NMRD study of biotinylated paramagnetic liposomes containing Gd-bis-SDA-DTPA or Gd-DMPE-DTPA. 2002 Inorganica Chim Acta 331: 151-157. (Year: 2002).*

Oliver et al. MAGfect: a novel liposome formulation for MRI labelling and visualization of cells. 2006 Org. Biomol Chem. 4: 3489-3497. (Year: 2006).*

Bhattacharya, S and Haldar, S, "Interactions Between Cholesterol and Lipids in Bilayer Membranes. Role of Lipid Headgroup and Hydrocarbon Chain-Backbone Linkage," Biochimica et Biophysica Acta 1467(1):39-53, Elsevier Publishing Company, Netherlands (Jul. 2000).

Caravan, P., et al., "Gadolinium(III) Chelates as MRI Contrast Agents: Structure, Dynamics, and Applications.," Chemical Reviews 99(9):2293-2352, American Chemical Society. United States (Sep. 1999).

Charrois, G.J and Allen, T.M, "Drug Release Rate Influences the Pharmacokinetics, Biodistribution, Therapeutic Activity, and Toxicity of Pegylated Liposomal Doxonbicin Formulations in Murine Breast Cancer," Biochimica et Biophysica Acta 1663(1-2):167-177, Elsevier Publishing Company, Netherlands (May 2004).

Choi, H., et al., "Iron Oxide Nanoparticles as Magnetic Resonance Contrast Agent for Tumor Imaging via Folate Receptor-targeted Delivery." Academic Radiology 11(9):996-1004. Association of University Radiologists, United States (Sep. 2004 ).

Gabizon, A., et al., "In Vivo Fate of Folate-targeted Polyethylene-glycol Liposomes in Tumor-bearing Mice," Clinical Cancer Research 9(17):6551-6559, The Association, United States (Dec. 2003).

Gabizon, A.A., et al., "Pros and Cons of tire Liposome Platform in Cancer Drug Targeting," Journal of Liposome Research 16(3):175-183. Informa Healthcare, England (2006).

Ghaghada, K.B., et al., "Folate Targeting of Drug Carriers: a Mathematical Model," Journal of Controlled Release 104(1):113-128, Elsevier Science Publishers, Netherlands (May 2005).

Gupta, Y., et al., "Design and Development of Folate Appended Liposomes for Enhanced Delivery of 5-fu to Tumor Cells," Journal of Drag Targeting 15(3):231-240. Informa Healthcare, England (Apr. 2007).

Henriksen, G., et al., "Preparation and Preclinical Assessment of Folate-conjugated, Radiolabelled Antibodies," Anticancer Research 25(1A):9-15, International Institute of Anticancer Research, Greece (Jan.-Feb. 2005).

Hilgenbrink, A.R and Low, P.S, "Folate Receptor-mediated Drug Targeting: From Therapeutics to Diagnostics," Journal of Pharmaceutical Sciences 94(10):2135-2146, Elsevier, United States (Oct. 2005).

(Continued)

*Primary Examiner* — Jennifer Lamberski
(74) *Attorney, Agent, or Firm* — McCarter & English, LLP; Beverly W. Lubil

(57) ABSTRACT

The present invention provides novel liposomes comprising Gd.DOTA.DSA (gadolinium (III) 2-{4,7-bis-carboxymethyl-10-[(N,N-distearylamidomethyl-N'-amido-methyl]-1, 4,7,10- =tetra-azacyclododec-1-yl}-acetic acid), characterised in that the liposome further comprises a neutral, fully saturated phospholipid component (e.g. DSPC (1,2-distearoyl-sn-glycero-3-phospocholine]), which are of particular use in the preparation of magnetic resonance contrast agents for enhancing a magnetic resonance image of tumours in a mammal.

21 Claims, 24 Drawing Sheets

(56) References Cited

OTHER PUBLICATIONS

Hofland, H.E., et al., "Folate-Targeted Gene Transfer in Vivo." Molecular Therapy 5(6):739-744, Cell Press, United States (Jun. 2002).
Iyer, A.K., et al., "Exploiting the Enhanced Permeability and Retention Effect for Tumor Targeting," Drug Discovery Today 11(17-18):812-818, Elsevier Science Ltd, England (Sep. 2006).
Kabalka, G.W., et al., "Gadolinium-Labeled Liposomes Containing Amphiphilic Gd-DTPA Derivatives of Varying Chain Length: Targeted MRI Contrast Enhancement Agents fertile Liver," Magnetic Resonance Imaging 9(3):373-377, Elsevier. Netherlands (1991).
Kamaly, N., et al., "A Novel Bimodal Lipidic Contrast Agent for Cellular Labelling and Tumour MRI," Organic and Biomolecular Chemistry 8(1):201-211, Royal Society of Chemistry', England (Jan. 2010).
Kamaly. N., et al., "Bimodal Paramagnetic and Fluorescent Liposomes for Cellular and Tumor Magnetic Resonance Imaging," Bioconjugate Chemistry 19(1):118-129, American Chemical Society (2008).
Kamaly, N., et al., "Folate Receptor Targeted Bimodal Liposomes for Tumor Magnetic Resonance Imaging," Bioconjugate Chemistry 20(4):648-655. American Chemical Society, United States (Apr. 2009).
Ke, C.Y., et al., "Folate-receptor-targeted Radionuclide Imaging Agents," Advanced Drug Delivery Reviews 56(8):1143-1160, Elsevier Science Publishers, Netherlands (Apr. 2004).
Kim, I.B., et al., "Use of a Folate-PPE Conjugate to Image Cancer Cells in Vitro," Bioconjugate Chemistry 18(3):815-820, American Chemical Society, United States (May-Jun. 2007).
Konda, S.D., et al., "Specific Targeting of Folate-dendrimer MRI Contrast Agents to the High Affinitv Folate Receptor Expressed in Ovarian Tumor Xenografts," Magma 12(2-3):104-113, Springer, Germany (May 2001).
Lian, T. and Ho, R.J., "Trends and Developments in Liposome Drug Delivery Systems," Journal of Pharmaceutical Sciences 90(6):667-680, Elsevier, United States (2001).
Low, P.S., et al., "Discovery and Development of Folic-acid-based Receptor Targeting for Imaging and Therapy of Cancer and Inflammatory Diseases," Accounts of Chemical Research 41(1):120-129, American Chemical Society, United States (Jan. 2008).
Maeda, H., et al., "Tumor Vascular Permeability and the EPR Effect in Macromolecular Therapeutics: a Review," Journal of Controlled Release 65(1-2):271-284, Elsevier Science Publishers, Netherlands (Mar. 2000).
Massoud, T.F and Gambhir, S.S. "Molecular Imaging in Living Subjects: Seeing Fundamental Biological Processes in a New Light," Genes & Development 17(5):545-580. Cold Spring Harbor Laboratory Press, United States (Mar. 2003).
Miller, A and Tanner, J.; "The Essentials of Chemical Biology", J. Wiley & Sons, 2008, Chapter 1, section 1.5, entitled "Macromolecular lipid assemblies", pp. 69-80.
Moghimi, S.M and Szebeni, J, "Stealth Liposomes and Long Circulating Nanoparticles: Critical Issues in Pharmacokinetics, Opsonization and Protein-binding Properties," Progress in Lipid Research 42(6):463-478, Pergamon, England (Nov. 2003).
Mulder, W.J., et al., "A Liposomal System for Contrast-Enhanced Magnetic Resonance Imaging of Molecular Targets," Bioconjugate Chemistry 15(4):799-806, American Chemical Society, United States (Jul.-Aug. 2004).
Muller, C., et al., "In Vitro and in Vivo Targeting of Different Folate Receptor-positive Cancer Cell Lines With a Novel 99mtc-radiofolate Tracer," European Journal of Nuclear Medicine and Molecular Imaging 33(10):1162-1170, Springer-Verlag Berlin, Germany (Oct. 2006).
Oliver, M., et al., "MAGfect: a Novel Liposome Formulation for MRI Labelling and Visualization of Cells," Organic & Biomolecular Chemistry 4(18):3489-3497, Royal Society of Chemistry, England (Sep. 2006).
Oyewumi, M.O., et al., "Comparison of Cell Uptake, Biodistribution and Tumor Retention of Folate-coated and PEG-coated Gadolinium Nanoparticles in Tumor-Bearing Mice," Journal of Controlled Release 95(3):613-626, Elsevier Science Publishers, Netherlands (Mar. 2004).
Parac-Vogt, T. N., et al., "Gadolinium DTPA-Monoamide Complexes Incorporated into Mixed Micelles as Possible MRI Contrast Agents," European Journal of Inorganic Chemistry 2004(17):3538-3543, (Sep. 2004).
Reddy, J.A., et al., "Targeting Therapeutic and Imaging Agents to Folate Receptor Positive Tumors," Current Pharmaceutical Biotechnology 6(2):131-150, Bentham Science Publishers, Netherlands (Apr. 2005).
Salazar, M.D and Ratnam, M, "The Folate Receptor: What Does It Promise in Tissue-targeted Therapeutics?," Cancer and Metastasis Reviews 26(1):141-152, Kluwer Academic, Netherlands (Mar. 2007).
Saul, J.M., et al., "A Dual-ligand Approach for Enhancing Targeting Selectivity of Therapeutic Nanocarriers," Journal of Controlled Release 114(3):277-287, Elsevier Science Publishers, Netherlands (Sep. 2006).
Scherphof, G. L., et al., "Modulation of Pharmacokinetic Behavior of Liposomes," Advanced Drug Delivery Reviews 24(2-3):179-191, Elsevier B.V (Mar. 1997).
Sega, E.I and Low. P.S, "Tumor Detection Using Folate Receptor-Targeted Imaging Agents," Cancer and Metastasis Reviews 27(4):655-664, Kluwer Academic, Netherlands (Dec. 2008).
Shah, K., et al., "Molecular Imaging of Gene Therapy for Cancer," Gene therapy 11(15):1175-1187, Nature Publishing Group, England (Aug. 2004).
Stevens, P.J., et al., "A Folate Receptor-targeted Lipid Nanoparticle Formulation for a Lipophilic Paclitaxel Prodrug," Pharmaceutical Research 21(12):2153-2157, Kluwer Academic/Plenum Publishers, United States (Dec. 2004).
Strikers, G.J., et al., "Relaxivity of Liposomal Paramagnetic MRI Contrast Agents," MAGMA 18(4):186-192, Springer, Germany (Sep. 2005).
Sudimack, J and Lee, R.J, "Targeted Drag Delivery via the Folate Receptor," Advanced Drag Delivery Reviews 41(2):147-162, Elsevier Science Publishers, Netherlands (Mar. 2000).
Sun, C., et al., "Folic Acid-PEG Conjugated Superparamagnetic Nanoparticles for Targeted Cellular Uptake and Detection by MRI," Journal of Biomedical Materials Research Part A 78(3):550-557, John Wiley & Sons, United States (Sep. 2006).
Tilcock, C., et al., "Liposomal Gd-DTPA: Preparation and Characterization of Relaxivity," Radiology 171(1):77-80, Radiological Society of North America, United States (Apr. 1989).
Torchilin, V.P, "Targeted Pharmaceutical Nanocarriers for Cancer Therapy and Imaging," The AAPS Journal 9(2):E128-E147, American Association of Pharmaceutical Scientists, United States (May 2007).
Unger. E.C., et al., "Clearance of Liposomal Gadolinium: in Vivo Decomplexation," Journal of Magnetic Resonance Imaging 1(6):689-693, Wiley-Liss, United States (Nov.-Dec. 1991).
Wang, S., et al., "Design and Synthesis of [111in]dtpa-folate for Use as a Tumor-targeted Radiopharmaceutical," Bioconjugate Chemistry 8(5):673-679, American Chemical Society, United States (Sep.-Oct. 1997).
Wang, Z.J., et al., "MR Imaging of Ovarian Tumors Using Folate-receptor-targeted Contrast Agents," Pediatric Radiology 38(5):529-537, Springer-Verlag, Germany (May 2008).
Wu, J., et al., "A Folate Receptor-targeted Liposomal Formulation for Paclitaxel," International Journal of Pharmaceutics 316(1-2):148-153, Elsevier/North-Holland Biomedical Press, Netherlands (Jun. 2006).
Wu, M., et al., "Expression of Folate Receptor Type Alpha in Relation to Cell Type, Malignancy, and Differentiation in Ovary, Uterus, and Cervix," Cancer Epidemiology, Biomarkers & Prevention 8(9):775-782, American Association for Cancer Research, United States (Sep. 1999).
Search Report for United Kingdom Patent Application No. GB0920304.3, dated Jun. 25, 2010.
International Search Report and Whitten Opinion for International Application No. PCT/GB2010/051925, European Patent Office, Rijswijk, Netherlands, dated Mar. 7, 2011.

* cited by examiner a b

| Dilution | Z-Avg, nm | PdI | Int-Pk, nm | Int% | Vol-Pk, nm | Vol% |
|---|---|---|---|---|---|---|
| 10x | 76.7 (1.3) | 0.155 (0.011) | 86.0 (3.5) | 99.0 (1.0) | 62.4 (1.5) | 99.4 (0.6) |
| 100x | 76.5 (0.5) | 0.157 (0.009) | 87.8 (3.5) | 99.3 (0.9) | 61.0 (1.2) | 99.6 (0.5) |
| 1000x | 89.0 (1.8) | 0.319 (0.035) | 97.5 (7.6) | 93.3 (2.1) | 60.5 (1.4) | 96.4 (0.8) |

| ID | Z-Avg (nm) | PdI | Int-Peak (nm) | %Int | Vol-Peak (nm) | %Vol |
|---|---|---|---|---|---|---|
| Bath-sonicated 0.45μm filtered | 100.4 (0.5) | 0.131 (0.014) | 115.8 (1.9) | 100 (0) | 87.1 (1.5) | 100 (0) |
| Bath-sonicated 0.20μm filtered | 99.5 (0.6) | 0.086 (0.017) | 109.5 (1.6) | 100 (0) | 90.5 (1.4) | 100 (0) |

| Sample | | $T_1$(MS) |
|---|---|---|
| | 0.5mM Gd.DOTA.DSA | 400 1 ± 15.92 |
| | 0.5mM DOTA.DSA | 2356 ± 112 588 |
| | Magnevist® | 371.0 ± 4.321 |
| | $H_2O$ | 2750 ± 121.8 |
| | 0.5mM Gd.DTPA.BSA | 687.5 ± 26.03 |
| | 0.5mM Gd.DTPA.BSA | 2760 ± 211.7 |

FIGURE 30

LIPOSOME NANOPARTICLES FOR TUMOR MAGNETIC RESONANCE IMAGING

FIELD OF THE INVENTION

The present invention relates to novel liposomes suitable for use in the preparation of a contrast agent for use in enhancing magnetic resonance imaging (MRI), particularly in enhancing magnetic resonance images of tumours.

BACKGROUND TO THE INVENTION

Cancer imaging is one of the most important disease areas where molecular imaging is set to play a major role, both in the detection of cancer and subsequent treatment. For effective cancer imaging by magnetic resonance imaging (MRI) there is a clear need to develop effective and biocompatible molecular imaging probes.[1,2] In this field, nanotechnology has a lot to offer as nanomedicine is set to make considerable contributions in the important areas of drug delivery, disease detection, and therapy. The application of nanotechnology platforms to cancer imaging has opened up opportunities for the use of multifunctional nanoparticle systems such as liposomes, in the study of cancer detection and therapy.

MRI is a clinical imaging modality that produces 3D opaque images of tissues containing water. Over 40% of clinical imaging worldwide today requires the injection of some form of MRI contrast agent. This is due to the fact that MRI suffers from an inherent lack of sensitivity and often in order to diagnose pathology correctly, a paramagnetic contrast agent is injected intravenously into patients to further enhance the magnetic resonance (MR) signal and hence site of disease. These agents consist of molecules which incorporate a paramagnetic metal ion, most commonly gadolinium or iron. Image improvement arises due the effect of the enhancement of longitudinal ($T_1$) or transverse ($T_2$) relaxation times of the surrounding bulk water protons by the coordinated metal ion. Contrast agents incorporating gadolinium increase both $1/T_1$ and $1/T_2$ but are generally used in $T_1$-weighted imaging where their $1/T_1$ effect is greater in tissue than their $1/T_2$ enhancement.[3] Iron containing agents, on the other hand, lead to more substantial increases in $1/T_2$ and are therefore visualised with $T_2$-weighted images. The use of gadolinium based MRI contrast agents produces a positive image enhancement (bright signal on image) and the use of iron agents leads to a negative image enhancement (darkening of image).

Gd.DTPA [gadolinium (III)-diethylenetriaminepentaacetate complex] (FIG. 1) was the first water soluble, renally excreteable contrast agent approved for clinical use by the FDA since mid 1988, and is currently routinely used under the commercial name Magnevist®[4]. FIG. 1 presents a few examples of the most commonly utilised contrast agents in the clinic.

These compounds are generally inert stable complexes where the metal ion is strongly chelated to the poly(aminocarboxylate) ligands. These types of agents are non-specific, mainly reside within the blood stream and also accumulate in the kidneys due to their glomerular filtration and are generally excreted un-metabolised. Nevertheless, their use in clinical MR imaging has great value as anatomical abnormalities such as gliomas and lesions within the brain can be visualised, since under normal physiological conditions these agents do not cross an intact blood brain barrier. Pathologies within the liver and other organs can also be visualised since these contrast agents rapidly accumulate into interstitial spaces and can therefore increase the signal to noise ratio, in such regions of increased fluid volume.

However, as these agents are non-specific and are cleared within a few hours of injection, their utility in MR imaging is limited to a short imaging time window and mainly, enhancement of the blood pool. Much effort has been made recently within the field of molecular imaging to improve the properties of MRI contrast agents, which has led to the use of polymers, dendrimers and various nanoparticles as Gd carriers. We have synthesized our own novel library of MRI active lipids. These lipids have then been used to formulate liposomes for tumour imaging.

Liposomes are composed of lipid constituents, with hydrophilic head groups and hydrophobic tail groups (FIG. 2). When hydrated, these lipids aggregate together to form self-assembled bilayer vesicles that enclose an aqueous compartment. Due to this aqueous cavity, they have traditionally been used as drug delivery vehicles, encapsulating water soluble drugs in order to improve drug pharmacokinetics. In addition, nucleic acids have also been condensed into liposome formulations for effective transfection and gene delivery. Despite these additional functionalities, liposomes were originally studied as models of biological membranes, and this is a key concept in the realisation of their biocompatibility.

The versatile nature of liposomes can be altered to change their interaction with various molecules or even larger structures such as cells. This can be done by altering the overall charge of the liposome surface by incorporating lipids with highly charged polar head groups in the liposome formulation, e.g. the incorporation of cationic lipids in the formulation produces cationic liposomes. Cationic lipids have been used to formulate liposome/DNA complexes (lipoplexes) used as gene delivery systems in vitro and in vivo.

Liposomes are typically characterised by their size, shape and lamellarity. They may be composed of a single bilayer (unilamellar), a few bilayers (oligolamellar), or multiple bilayers (multilamellar). The rigidity of the membrane can be modified with the use of suitable lipids; and the fluidity of the membrane may be varied by using phospholipids with high or low phase transition temperatures. In general lipid derivatives of stearic acids (fully saturated C18 lipidic chains) bestow rigidity and impermeability to the membrane, whilst lipid derivatives of oleic acid (unsaturated C18 lipidic chains) result in a more permeable and less stable lipid bilayer.

By incorporating gadolinium lipids into the membranes of liposomes they can be rendered MRI visible and systems with a better control of size can be obtained.[5] Liposomes are well suited as carriers of a high payload of gadolinium into cells. The incorporation of amphipathic gadolinium complexes into liposomal membranes has yielded paramagnetically labelled liposomes which significantly enhance proton relaxivity. These paramagnetic liposomes have been used in a number of investigations including that of cellular labelling and tracking.[6] The incorporation of gadolinium lipids into liposome formulations was demonstrated by Kabalka et al. over 20 years ago and the gadolinium lipid Gd.DTPA.BSA [gadolinium(III).diethylenetriaminopentraacetic acid-bis(stearylamide)] used in their studies is frequently used to prepare paramagnetic liposomes today.[7]

The ability to tune liposome size, surface charge and specificity allows for potential pathological imaging such as the imaging of solid tumours in vivo. This tuning of liposomes is made possible by adjusting the composition of the liposome formulation. Surface charges tending to neutrality are best suited for in vivo purposes in order to reduce the recognition of liposome particles by plasma proteins and the reticuloendothelial system (RES). This can be achieved through the inclusion of charge neutral lipids in the liposome formulation.

Previous work has shown the novel gadolinium lipid Gd.DOTA.Chol (gadolinium(III). 1,4,7,10-tetraazacyclododecane-N,N',N'',N'''-tetraacetate-cholesterol) (see FIG. 3) to be an effective MR signal enhancer, and MAGfect a liposome formulation containing this gadolinium lipid to be an efficient cellular dual labelling and transfection vehicle.[6]

Although a relatively effective cellular labelling lipid, formulation of high liposome concentrations using this lipid has been found to be problematic, perhaps due to the poor anchoring of the cholesterol tail in the liposome bilayers at high concentrations. Therefore, due to this limitation, the need to provide a more robust membrane anchor designed for in vivo applications where higher concentrations of liposome were required led to the investigation of an alternative saturated alkyl chain moiety in place of the cholesterol anchor. For this purpose a paramagnetic lipid Gd.DOTA.DSA (gadolinium (III) 2-{4,7-bis-carboxymethyl-10-[(N, N-distearylamidomethyl-N'-amido-methyl]-1,4,7,10-tetra-azacyclododec-1-yl}-acetic acid) (see FIG. 4) was synthesised using a combination of solution and solid phase chemistries.

The DOTA chelate was conjugated to the lipid via a stable yet biodegradable amide functional group. This gadolinium lipid was also designed with a five-atom spacer between the gadolinium chelator and lipidic alkyl chain moieties. This spacing between the head group and the lipidic alkyl tail was considered to be optimal in order to ensure maximum exposure of the gadolinium chelate to water on the hydrophilic surface of the liposome particles. Furthermore, this gadolinium lipid was also designed with the DOTA ligand rather than the more frequently used DTPA [diethylenetriaminopentaacetic acid], since the former macrocyclic ligand is considered to be a more effective chelator of gadolinium, able to retain the metal ion even in the acidic environment of the endosome.[8] The FDA approved Gd.DOTA chelate was chosen, since due to their higher stability constants, DOTA based conjugates are known to be more stable in vivo in comparison to DTPA ligands.

MRI Efficacy

In order to establish the relaxation properties of Gd.DOTA.DSA, MRI studies of the lipid in aqueous solution were performed and $T_1$ values and relaxivity parameters generated in milliseconds. The efficacy of gadolinium lipid Gd.DOTA.DSA was compared to the clinical contrast agent Magnevist® (Schering A G) and Gd.DTPA.BSA (see Table 1)(FIG. 30), and was found to compare favourably at the clinically relevant dose. These data also showed Gd.DOTA.DSA to have a comparable, if slightly better, $T_1$ relaxation than the widely used Gd.DTPA.BSA lipid. A standard $T_1$ saturation recovery method (spin echo sequence) was used to determine $T_1$ values (according to Eq. 1), where x is TR (time to repeat), and Si is the measured signal for a given TR.

$$S_i=S_0(1-e^{(-x/T_1)})$$

Equation 1. $T_1$ saturation recovery equation used to determine $T_1$ values.

It has been found that using Gd.DOTA.DSA it is possible to successfully formulate both cationic and neutral liposomes, and these liposomes have been studied for their stability, in vitro toxicity, in vitro transfection and in vivo tumour imaging capabilities [see Kamaly et al 2009: Bioconjug Chem. 2009 Apr. 20(4):648-55, and Kamaly et al 2008: Bioconjug Chem. 2008 Jan. 19(1):118-29. Epub 2007 Nov. 7]. Kamaly et al have further developed two neutral PEGylated liposomes which have superior tumour MR signal enhancement capabilities in vivo, in addition to added stability. These particles also incorporate Gd.DOTA.DSA. These liposomes contain the unsaturated phospholid DOPC (1,2-dioleoyl-sn-glycero-3-phosphocholine), the structure of which is as follows:

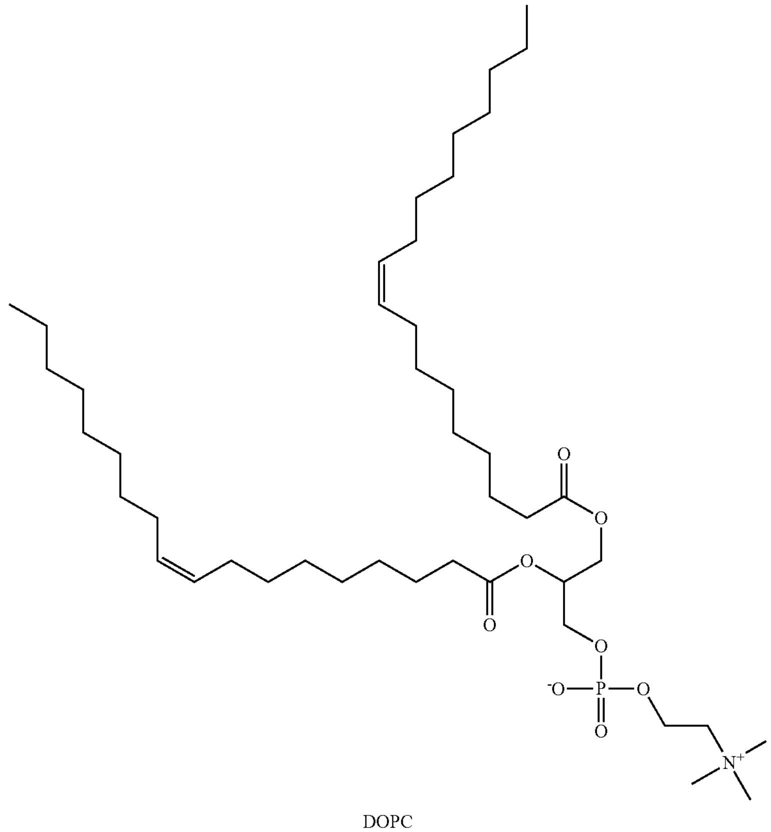

DOPC

However, there is still a need for robust and stable lipsome nanoparticles comprising gadolinium which have superior tumour MR signal enhancement capabilities in vivo. Specifically, there is a need for liposomes whose properties are such that they optimise accumulation of said liposomes in solid tumours while minimising their accumulation in organs of the body such as the liver, thus enhancing their MR signal enhancing effect while greatly reducing the toxicity of these gadolinium liposomes and improving their safety. We have developed novel liposomes comprising Gd.DOTA.DSA which meet these needs.

DESCRIPTION OF THE INVENTION

In a first aspect of the present invention there is provided (1) a liposome comprising Gd.DOTA.DSA (gadolinium (III) 2-{4,7-bis-carboxymethyl-10-[(N,N-distearylamidomethyl-N'-amido-methyl]-1,4,7,10-tetra-azacyclododec-1-yl}-acetic acid), characterised in that said liposome further comprises a neutral, fully saturated phospholipid component.

Preferred aspects of the liposome of this first aspect of the invention include:

(2) a liposome according to (1), wherein said fully saturated phospholipid component is a 1,2-di($C_{12}$-$C_{20}$ saturated lipid)-sn-glycero-3-phosphocholine, wherein the saturated lipid groups can be the same or different from each other.

(3) a liposome according to (1), wherein said fully saturated phospholipid component is DSPC (1,2-distearoyl-sn-glycero-3-phosphocholine).

(4) a liposome according to any one of (1) to (3), wherein said liposome further comprises cholesterol.

(5) a liposome according to any one of (1) to (4), wherein said liposome further comprises a polyethylene glycol-phospholipid component.

(6) a liposome according to (5), wherein said polyethylene glycol-phospholipid is DSPE-PEG(2000) [distearoylphosphatidylethanolamine-polyethylene glycol (2000)].

(7) a liposome according to any one of (1) to (6), wherein the amount of Gd.DOTA.DSA in said liposome is from 29 to 31 mol % of the total liposome formulation.

(8) a liposome according to any one of (1) to (6), wherein the amount of Gd.DOTA.DSA in said liposome is 30 mol % of the total liposome formulation.

(9) a liposome according to any one of (1) to (8), wherein the amount of fully saturated phospholipid component in said liposome is from 32 to 34 mol % of the total liposome formulation.

(10) a liposome according to anyone of (1) to (8), wherein the amount of fully saturated phospholipid component in said liposome is 33 mol % of the total liposome formulation.

(11) a liposome according to anyone of (1) to (10), wherein the amount of cholesterol in said liposome is from 29 to 31 mol % of the total liposome formulation.

(12) a liposome according to anyone of (1) to (10), wherein the amount of cholesterol in said liposome is 30 mol % of the total liposome formulation.

(13) a liposome according to anyone of (1) to (12), wherein the amount of said polyethylene glycol-phospholipid component in said liposome is 5-8 mol % of the total liposome formulation.

(14) a liposome according to anyone of (1) to (12), wherein the amount of said polyethylene glycol-phospholipid component in said liposome is 7 mol % of the total liposome formulation.

(15) a liposome according to anyone of (1) to (14), wherein said liposome has an average particle size at 10× dilution in phosphate buffer solution of less than or equal to 100 nm.

(16) a liposome according to anyone of (1) to (14), wherein said liposome has an average particle size at 10× dilution in phosphate buffer solution of less than or equal to 80 nm.

(17) a liposome according to (1), wherein said liposome comprises Gd.DOTA.DSA, cholesterol, DSPC and DSPE-PEG(2000).

(18) a liposome according to (17) wherein Gd.DOTA.DSA, cholesterol, DSPC and DSPE-PEG(2000) are present in the ratio 30:33:30:7 mol % respectively in said liposome formulation.

In a second aspect of the present invention there is provided:

(19) a liposome according to any one of (1) to (17), wherein said liposome further comprises a tumour targeting agent.

Preferred liposomes comprising a tumour targeting agent include:

(20) a liposome according to (19), wherein said tumour targeting agent comprises a ligand for a receptor that is over-expressed in tumour cells relative to the expression of said receptors in the cells of non-tumourous tissue of mammals.

(21) a liposome according to (20), wherein said tumour targeting agent comprises a folate moiety.

(22) a liposome according to (20), wherein said tumour targeting agent is a phospholipid-polyethylene glycol-folate compound.

(23) a liposome according to (22), wherein said phospholipid-polyethylene glycol-folate compound is DSPE-PEG (2000)-Folate [distearoylphosphatidylethanolamine-polyethylene glycol (2000)-folate].

(24) a liposome according to any one of (21) to (23), wherein the amount of said folate moiety present in said liposome is 1-2 mol % of the total liposome formulation.

(25) a liposome according to (19), wherein said liposome comprises Gd.DOTA.DSA, cholesterol, DSPC, DSPE-PEG(2000) and DSPE-PEG(2000)-Folate.

(26) a liposome according to (25), wherein Gd.DOTA.DSA, cholesterol, DSPC, DSPE-PEG(2000) and DSPE-PEG (2000)-Folate are present in the ratio 30:33:30:5.5:1.5 mol % respectively in said liposome formulation.

In a third aspect of the present invention, there is provided:

(27) a magnetic resonance contrast agent, comprising liposomes according to any one of (1) to (26) and a pharmaceutically acceptable carrier.

In a preferred embodiment, there is provided:

(28) a magnetic resonance contrast agent according to (27), wherein said pharmaceutically acceptable carrier is an aqueous carrier.

In a fourth aspect of the present invention, there is provided:

(29) a magnetic resonance contrast agent according to (27) or (28) for use in medicine, e.g. in diagnosis.

In a fifth aspect of the present invention, there is provided:

(30) use of a liposome according to any one of (1) to (26) in the preparation of a magnetic resonance contrast agent for enhancing magnetic resonance images of organs and organ structures in a mammal.

Preferred aspects of this fifth embodiment include:

(31) use according to (30) in the preparation of a magnetic resonance contrast agent for enhancing a magnetic resonance image of a tumour in a mammal.

(32) use according to (30) or (31), wherein the concentration of said liposomes in said magnetic resonance contrast agent is 1-50 mg/mL, more preferably 1-30 mg/mL.

In a sixth aspect of the present invention, there is provided:

(33) a method of magnetic resonance imaging of an organ or organ structure in a mammal, comprising the steps of:

(a) administering the magnetic resonance contrast agent according to (27) or (28) to a patient; and (b) taking images of the organ of interest in the patient.

Preferred aspects of this sixth embodiment include:

(34) a method according to (33), wherein said magnetic resonance contrast agent is used for enhancing a magnetic resonance image of a tumour in a mammal.

(35) a method according to (33) or (34), wherein the concentration of liposomes in said magnetic resonance contrast agent is 1-50 mg/mL, more preferably 1-30 mg/mL.

In a seventh aspect of the present invention, there is provided:

(36) a method of magnetic resonance imaging of an organ or organ structure in a mammal pre-administered with the magnetic contrast agent according to (27) or (28) comprising the step of:

(i) taking images of the organ of interest in the patient.

In an eigth aspect of the present invention, there is provided:

(37) a method of making a liposome according to (1) to (26) comprising mixing a solution of Gd.DOTA.DSA (gadolinium (III) 2-{4,7-bis-carboxymethyl-10-[(N,N-distearylamidomethyl-N'-amido-methyl]-1,4,7,10-tetra-azacyclododec-1-yl}- acetic acid) and a solution of a neutral, fully saturated phospholipid.

A preferred aspect of the eigth embodiment includes:

(38) drying the mixture (e.g. in vacuo) and optionally rehydrating the resulting liposome.

In a ninth aspect of the present invention, there is provided:

(39) a method of making a magnetic contrast agent according to (27) or (28) comprising mixing a liposome of (1) to (26) and a pharmaceutically acceptable carrier.

Preferred aspects of the eigth and ninth embodiments are the same as those listed above in relation to the first, second and third aspects.

Detailed Description of the Invention

We will now discuss the present invention in further detail.

BRIEF DESCRIPTION OF THE DRAWINGS

The present invention may also be further understood by reference to FIGS. 1 to 30, wherein:

FIG. 30 presents relaxation values for the synthesised Gd lipids in addition to relevant controls; where $T_1$ represents values and images of Gd.DOTA.DSA and Gd.DTPA.BSA with relative controls.

The promising $T_1$ relaxation data of Gd.DOTA.DSA led to the development of gadolinium liposome formulations using Gd.DOTA.DSA, for systemic circulation in vivo, with the aim of tumour imaging by MRI, utilising the widely reported enhanced permeation and retention (EPR) effect. This led to the development of the novel Gd.DOTA.DSA liposome systems of the present invention which are characterised in that said liposome further comprises a neutral, fully saturated phospholipid component.

We have surprisingly found that by the incorporation of a neutral, fully saturated phospholipid component into the Gd.DOTA.DSA liposome systems of the present invention, the resulting liposomes are smaller and give more homogenous liposome preparations which have ideal properties for use in the preparation of magnetic resonance contrast agents as a result.

Appropriate neutral, fully saturated phospholipids suitable for use in the construction of Gd.DOTA.DSA liposomes of the present invention are typically 1,2-di($C_{12}$-$C_{20}$ saturated lipid)-sn-glycero-3-phosphocholines. More preferred examples include 1,2-distearoyl-sn-glycero-3-phosphocholine (DSPC) or 1,2-dimyristoyl-sn-glycero-3-phosphocholine (DMPC) lipids. 1,2-distearoyl-sn-glycero-3-phospocholine (DSPC) is most preferred. Typically, the amount of fully saturated phospholipid component in said liposome is from 32 to 34 mol % of the total liposome formulation, and most preferably it is 33 mol %. Typically, the amount of Gd.DOTA.DSA component in said liposome is from 29 to 31 mol % of the total liposome formulation, and most preferably it is 30 mol %.

Figure 7:
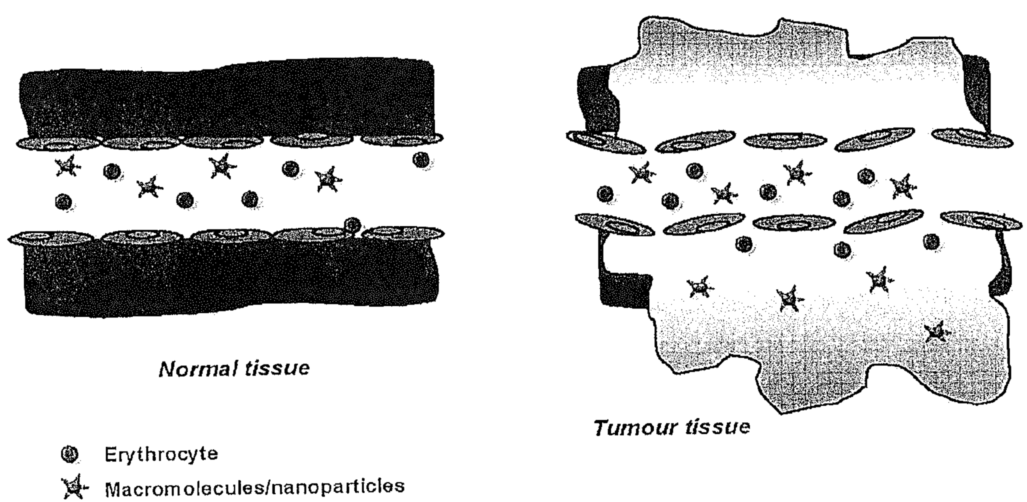
FIG. 7 depicts the EPR, where normal tissue does not have endothelial gaps wide enough to allow for macromolecular or nanoparticulate agents to leak into the extracellular tissue lining blood vessels, whereas tumour tissue has a disrupted endothelial layer, allowing for larger particles to “seep” into the tumour extracellular domain.

Typically, the liposomes have a size of 100 nm or less. By carefully nanoengineering the liposomes in this way to ensure that their size remains below 100 nm, this size range is considered optimal for the accumulation of liposomes in solid tumours due to the characteristics of tumour tissue. Tumour tissue is considered to possess a universal affinity for macromolecular agents, termed the enhanced permeation and retention effect (EPR), whereby macromolecular agents accumulate in tumour tissue. EPR was first introduced by Maeda et al.,[13] here; it is believed that tumour properties such as increased angiogenesis, a heterogeneous and destructive vascular infrastructure, impaired lymphatic drainage and a "leaky" endothelial layer are all factors that contribute to the accumulation of macromolecular structures within tumour tissue (see FIG. 7). As explained and exemplified further below, this provides particular, substantial advantages over the prior art MRI active liposomes and non-liposome paramagnetic contrasting agents as a result.

The EPR effect has become a standard model for the targeting of macromolecular drugs and polymeric or liposomal macromolecules to tumours. These agents are easily adapted for the imaging of tumours through their modification to include an imaging probe or moiety for signal localisation. The key mechanism here, being the retention of macromolecules in solid tumours, in contrast to low-molecular weight agents, such as Gd.DTPA (Magnevist™) which are re-circulated into blood through diffusion and cleared through the kidneys in relatively short periods post injection. This retention effect or particle accumulation within tumour tissue is also referred to as passive-targeting, and it has been shown that due to this effective phenomena very high levels (10-50 fold) of polymeric drugs can accumulate at tumour sites within a few days.[14] The mechanism of tumour accumulation of nanoparticles in tumour tissue has been established as the extravasation of large molecules through the disrupted endothelium lining tumour blood vessels. In addition to complying with the tumour extravasation size threshold, a further reason for liposome size to remain within the 100 nm range for in vivo injections is due to clearance of large liposomes through the liver. Large liposomes are taken up by liver cells which include hepatocytes and Kupffer cells, liposomal particles may accumulate in liver or spleen tissue due to the larger endothelial lining in these organs.

Figure 10:
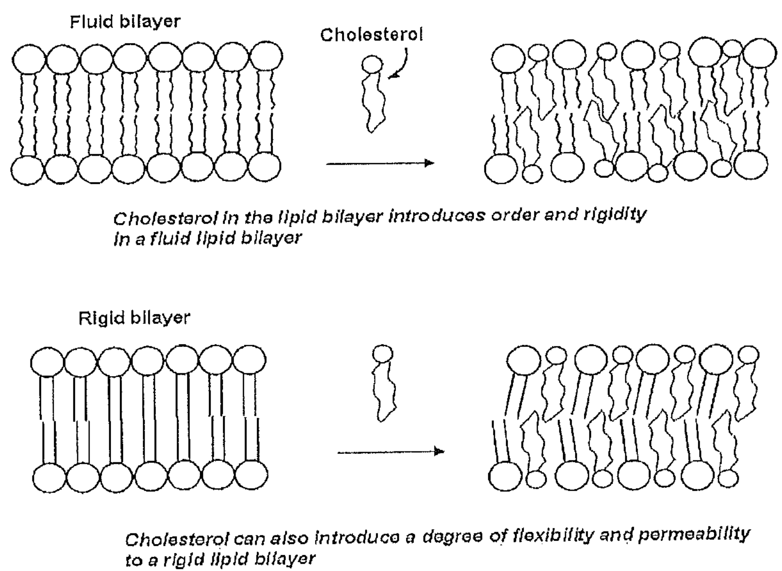
FIG. 10 shows the influence of cholesterol lipid on liposome bilayer permeability and rigidity.

Cholesterol may preferably be incorporated into the formulation since this lipid induces diverse effects on the liposomal bilayer. Cholesterol has been shown to increase the head group spacing in liposome formulations and stabilise the resulting bilayer membranes.[9] Here, cholesterol presence in the liposome formulation controls membrane permeability of both fluid and rigid bilayers by inducing conformational ordering of the lipid chains (FIG. 10). In addition, cholesterol can reduce serum induced aggregation as a direct result of its neutral charge.[10] Typically, the amount of cholesterol component in said liposome is from 29 to 31 mol % of the total liposome formulation, and most preferably it is 30 mol %.

In order to prolong the circulation time of the liposome nanoparticles to ensure maximum tumour exposure, polyethylene glycol (PEG) may also be anchored into the liposome bilayer using a polyethylene glycol-phospholipid tethered construct. Examples of preferred polyethylene glycol-phospholipids for use in the liposomes of the invention include DSPE-PEG(2000) [distearoylphosphatidylethanolamine-polyethylene glycol (2000)]. It has been shown that liposomes bearing a surface decorated with the neutral hydrophilic PEG polymer benefit from prolonged circulation times with half lives reported from 2 to 24 h in rodents, and as high as 45 h in humans.[11] The theory here is that surface-grafted PEG liposomes have reduced uptake by liver cells as the liposomes are not effectively bound by plasma proteins.[12] These liposomes are also referred to as sterically stabilised liposomes. Here, the PEG layer sterically inhibits both electrostatic and hydrophobic interactions of plasma components with the liposome bilayer. Typically, the amount of polyethylene glycol-phospholipid component in said liposome is from 5 to 8 mol % of the total liposome formulation, and most preferably it is 7 mol %.

For in vivo purposes, fully saturated phospholipids with neutral head groups have been incorporated in the liposome formulation; as described above these include but are not limited to; 1,2-distearoyl-sn-glycero-3-phospocholine (DSPC) or 1,2-dimyristoyl-sn-glycero-3-phosphocholine (DMPC) lipids. The utilisation of neutral lipids in addition to the incorporation of between 5-10 molar ratios of a PEGylated lipid in the liposome formulation, provides steric stabilisation and protection from blood plasma proteins such as opsonins, and leads to the reduction of Kupffer cell uptake. It is thought that stabilisation occurs by the formation of highly hydrated shields of polymer molecules around the liposome surface. Due to this "shielding" characteristic, these types of liposomes are often referred to as "Stealth" liposomes.

In a further embodiment of the present invention, the liposomes of the present invention may further incorporate a tumour targeting agent. Liposomes of the present invention comprising a tumour targeting agent typically comprise a ligand for a receptor that is over-expressed in tumour cells relative to the expression of said receptors in the cells of non-tumourous tissue of mammals.

One example of such a tumour targeting agent is one which comprises a folate moiety. In preferred examples of the present invention, the tumour targeting agent is a phospholipid-polyethylene glycol-folate compound. More preferably the phospholipid-polyethylene glycol-folate compound is DSPE-PEG(2000)-Folate [distearoylphosphatidylethanolamine-polyethylene glycol (2000)-folate].

Typically, the amount of the folate moiety present in the liposome is 1-2 mol % of the total liposome formulation.

As an example of a tumour targeting agents folate is a good example of such a targeting moiety; as folate-based targeting systems present an effective means of selectively delivering therapeutic or imaging agents to tumours.[15] It has been shown that aggressive or undifferentiated tumours at an advanced stage have an increased folate receptor (FR) density, indicating that cancer therapy could benefit from the broad approach that FR mediated drug delivery offers.[16] The FR is over-expressed in several cancer types, such as brain, kidney, lung and breast cancers and in particular, in epithelial carcinomas such as ovarian cancers.[17] The FR ligand, folate (or folic acid), is a vitamin that is used for the biosynthesis of nucleotides and is utilized in high levels to meet the needs of proliferating cancer cells.[18]

In addition to numerous drug delivery efforts, folate-targeted technology has been successfully applied to radio-imaging of therapeutic agents,[19] fluorescence imaging of cancer cells,[20] MRI contrast agents,[21] and gadolinium liposomes.[22] Choi et al., have demonstrated the use of folate-targeted iron oxide nanoparticles for the imaging of induced KB tumours and showed these particles to have a 38% signal intensity increase compared to controls.[23] Successful tumour MRI with a non-targeted bimodal liposomal contrast agent was shown recently, whereby bimodal paramagnetic and fluorescent liposomes of ~100 nm in size were seen to accumulate in a mouse xenograft model of ovarian cancer.[24] Liposomes are able to accumulate within tumour tissue due to the widely reported enhanced permeation and retention effect (EPR) which relies on the passive accumulation of colloidal macromolecules of ~40 kDa and above in tumours.[25] The EPR effect arises due to aberrant tumour endothelium, which as a result of its "leakiness" allows the penetration of nanoparticles into tumour tissue. Liposome accumulation in tumour tissue could be improved through the use of receptor targeting moieties that are either post-conjugated to the surface of liposomes, or are attached to lipids that become incorporated within the liposomal bilayer. Since FR binding affinity ($Kd=1\times1^{-10}$ M) does not appear to be affected when its ligand, folate is conjugated to an imaging agent or therapeutic moiety via its γ-carboxyl,[26] a folate ligand tethered onto the distal end of a lipidic PEG amphiphile allows for the development of a FR targeted liposomal system.

The human nasopharyngeal KB carcinoma cell line is considered to have the highest level of FR expression, yet the number of cases for this cancer are low in comparison to ovarian cancer which has the highest frequency (>90% of cases).[27] In particular, the α-FR isoform which is a glycosyl phosphatidylinositol (GPI)-anchored membrane protein is highly expressed in ovarian carcinoma.[28] Additionally, the α-FR isoform has also been shown to have specific biomarker value, aiding in the identification of metastatic tumour site origin.[29] Therefore, we were interested in using this receptor in order to test the efficacy of folate targeted bimodal liposomes for the imaging of ovarian tumours using MRI. Folate-based liposomal drug delivery has been studied extensively,[30] however, the rate-enhancing effect of liposome accumulation in tumours due to folate targeting has not been studied dynamically in real-time to a great extent. Effective tumour signal enhancement was anticipated since the FR is expressed in significantly lower amounts in normal tissue, limited mainly to kidney tubuli, lung epithelium, and placenta tissue.[31] To asses the value of the addition of a targeting ligand on the rate and extent of accumulation of liposomes in solid tumours, in the present invention FR targeted bimodal fluorescent and paramagnetic liposomes have been formulated and compared to non-targeted liposomes by both MRI and fluorescence microscopy. We have found that they give remarkably good results with low toxicity, excellent targeted MR signal enhancement and, after rapid accumulation in the tumour initially, a quick and natural clearance of the contrast agents from the body thereafter.

In a third aspect of the present invention, there is also provided a magnetic resonance contrast agent, which comprises liposomes according to any one of the first and second aspects of the present invention and a pharmaceutically acceptable carrier. Typically, the pharmaceutically acceptable carrier is an aqueous carrier such as a HEPES [(4-(2-hydroxyethyl)-1-piperazineethanesulfonic acid] buffered solution.

In a fourth aspect of the present invention, there is provided a magnetic resonance agent according to the third aspect for use in medicine, preferably for use in diagnosis and particularly preferably for use in imaging organs and organ structures (e.g. tumours).

In a fifth aspect of the present invention, there is provided use of a liposome according to any one of the first and second aspects of the invention in the preparation of a magnetic resonance contrast agent for enhancing magnetic resonance images of organs and organ structures in a mammal. The liposomes of the present invention are of particular use in the preparation of a magnetic resonance contrast agent for enhancing a magnetic resonance image of a tumour in a mammal.

As already described above, and further exemplified below, the paramagnetic liposomes of the present invention have superior properties due to their optimal size (increased accumulation in tumours due to the EPR effect and reduced liver toxicity due to reduced uptake by Kupffer cells), greater stability, stronger gadolinium chelation while their non-ionic nature reduces the physichochemical consequences that have previously been observed with ionic gadolinium contrast agents wherein an excess of negative charge leads to competitive reactions in vivo and displacement of $Gd^{3+}$. As a consequence, the magnetic resonance contrast agents of the present invention provide substantial and surprising advantages over the prior art paramagnetic gadolinium contrast agents as they have excellent image enhancement ability while at the same time showing a much improved safety profile owing to the reduced dose of gadolinium that is required as the gadolinium liposomes of the present invention gradually accumulate in tumour tissues without accumulating in other organs, particularly the liver. As a result of the greater effectiveness combined with the lower toxicity, the contrast agents of the present invention can offer a wider scope of magnetic resonance directed imaging in the clinic than the agents known to date.

Typically, the concentration of the liposomes in the magnetic resonance contrast agents of the invention is 1-50 mg/mL, more preferably 1-30 mg/mL, but the invention is not limited to these ranges. Examples of a pharmaceutically acceptable carrier for use in the preparation of the magnetic resonance contrast agents is an aqueous carrier such as a HEPES.

In a sixth aspect of the present invention, there is also provided a method of magnetic resonance imaging of an organ or organ structure in a mammal, comprising the steps of:

(a) administering the magnetic resonance contrast agent according to the third aspect of the present invention to a patient; and (b) taking images of the organ of interest in the patient.

Again, typically the method is used for enhancing a magnetic resonance image of a tumour in a mammal. We typically use a concentration of liposomes in the magnetic resonance contrast agent of 1-50 mg/mL, more preferably 1-30 mg/mL, but the invention is not limited to this range.

The present invention may be further understood by reference to the following examples.

EXAMPLES

Example 1 Liposome A

Figure 8:
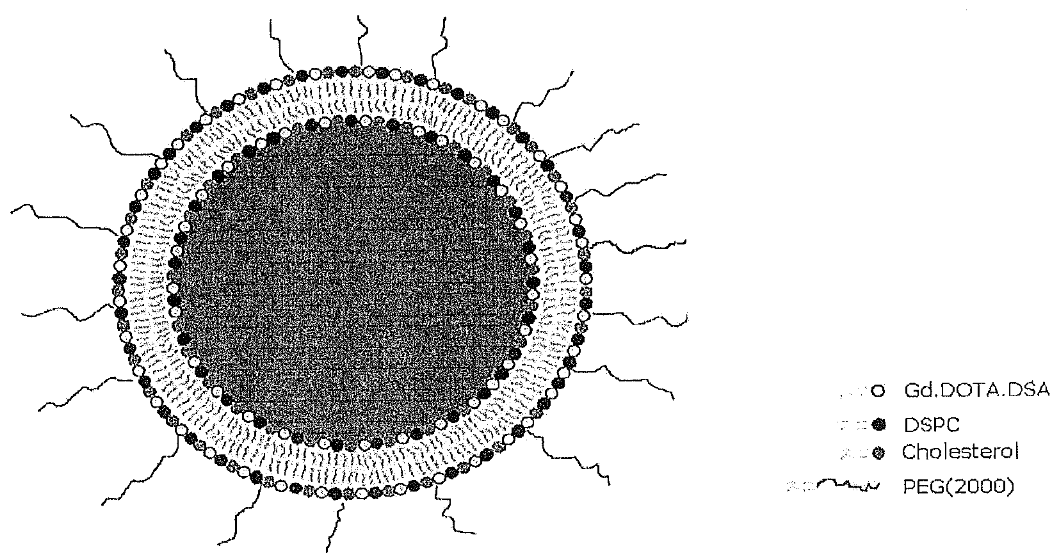
FIG. 8 provides a depiction of one of the preferred liposomes of the invention, liposome A, a novel MRI active liposome with tumour imaging utility.

Liposome A is depicted in FIG. 8. Liposome A is a novel MRI active liposome with tumour imaging ability, as we shall demonstrate below.

The Liposome A formulation consists of Gd.DOTA.DSA/DSPC/Cholesterol/DSPE_PEG2000: 30/33/30/7 mol %. For pre-clinical histology studies, a 1 mol % DOPE-Rhodamine is also added to the formulation and 32 mol % of DSPC is used.

Figure 9:
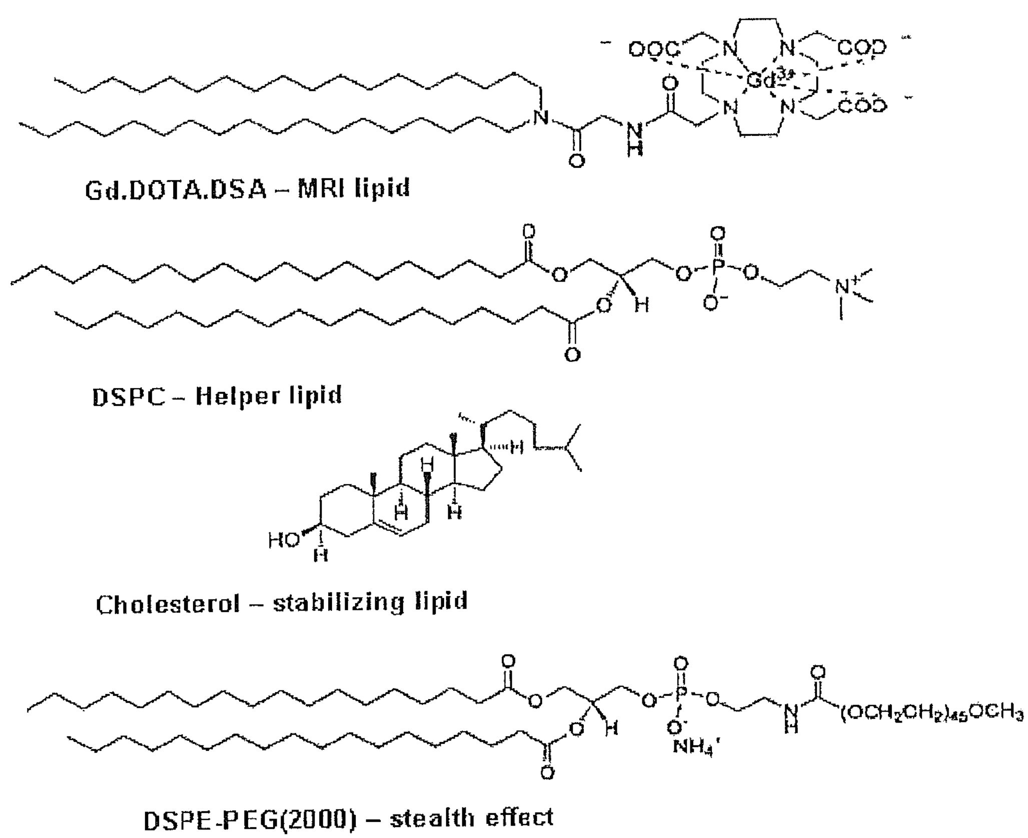
FIG. 9 depicts the structures of lipids forming one of the preferred liposomes of the invention, liposome A.

Liposome A was developed to observe signal enhancement of tumour tissue in vivo by MRI. The structures of the lipids comprising this liposome system are shown in FIG. 9. MRI signal enhancement is achieved by incorporating the paramagnetic lipid Gd.DOTA.DSA into the liposome formulation.

Liposome A Characterization

Figure 11:
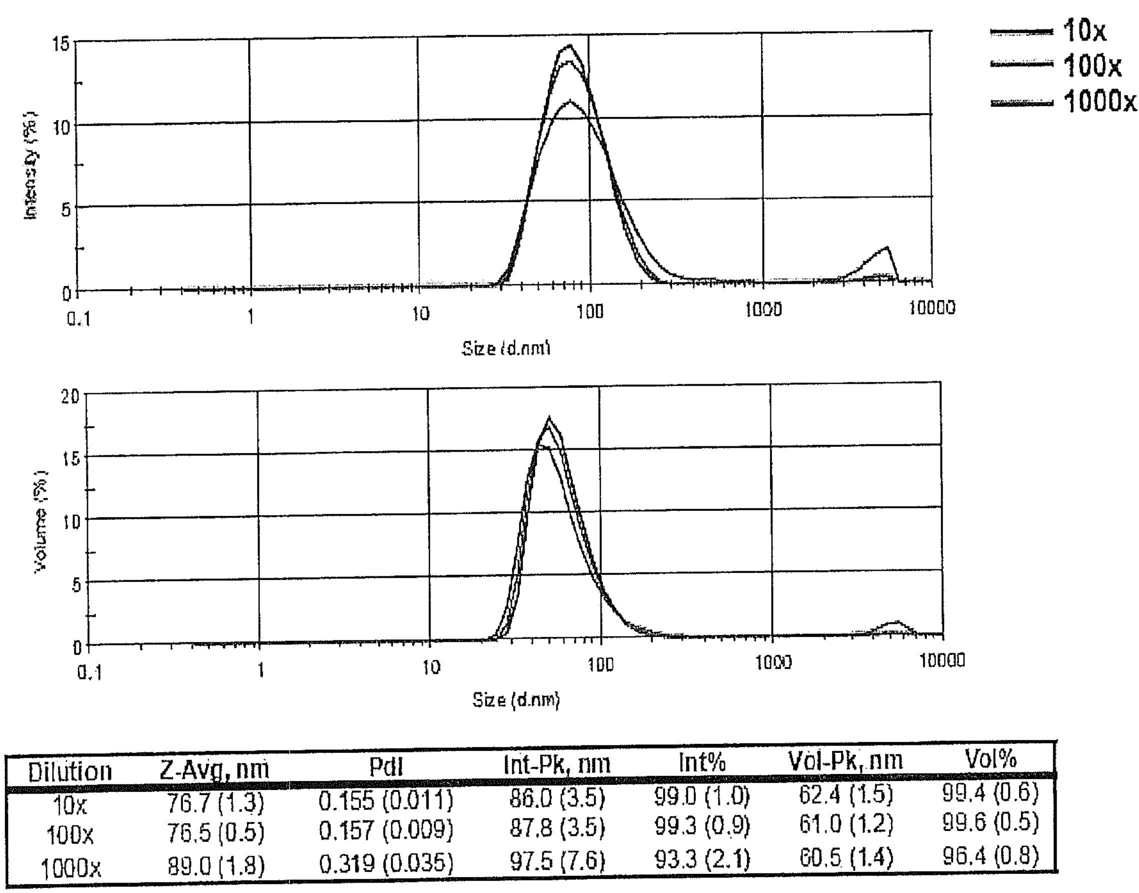
FIG. 11 shows the size distribution of the Liposome A particles.

Prior to toxicity assays, the size distribution of the particles was measured as per FIG. 11. In FIG. 11, the Liposome A particle sizes in various PBS dilutions are shown in the bottom graph while those of the control particle are shown in the top graph. The Liposome A formulation consists of Gd.DOTA.DSA/DSPC/Cholesterol/DSPE_PEG2000:30/33/30/7 mol % and the control nanoparticle is DOTA.DSA/DSPC/Cholesterol/DSPE_PEG2000:30/33/30/7 mol %. NB: The peaks at 1000 nm+ are removed post filtration through 0.2 μm filters (data not shown).

Both Liposome A and the control particle (no Gd chelated with the DOTA head group) were extremely stable, and were sized below 100 nm at various dilutions in PBS. The particle also had a very low polydispersity index, indicating a uniform and homogenous sample.

The measured sizes for Liposome A are smaller than previously published DOPC liposomes, and the polydispersity index (PdI) is also much lower than those measured for the same formulation containing DOPC (see Table 2). This indicates that the new DSPC formulation offers a smaller size distribution, which is more favourable for liver clearance of the liposomes and gradual accumulation within tumour tissue, and also a lower polydispersity index confirms a more homogenous and uniform liposome sample.

TABLE 2

Neutral PEGylated liposomes formulated with DOPC.

| Liposome Formulation (mol %) | | | | | | |
|---|---|---|---|---|---|---|
| Gd.DOTA.DSA | DOPC | Cholesterol | DOPE-Rhodamine | DSPE-$PEG_{2000}$ | Initial size (nm) | PI |
| 30 | 34 | 30 | 1 | 5 | 104.9 ± 34.6 | 0.420 |
| 30 | 33 | 30 | 1 | 6 | 114.6 ± 45.3 | 0.201 |
| 30 | 32 | 30 | 1 | 7 | 104.3 ± 36.8 | 0.309 |

In Vitro Toxicological Investigations

The in vitro toxicity of Liposome A and the control nanoparticle of the same composition but without Gd chelated in the DOTA macrocycle was assessed using the MTT and LDH toxicity assays. The liposomes were formulated in buffer [20 mM HEPES (4-(2-hydroxyethyl)-1-piperazineethanesulfonic acid], pH 6.8, 150 mM NaCl) at a total concentration of 25 mg $mL^{-1}$.

MTT Cell Viability Assay

The determination of cellular proliferation and viability are key areas assessed for in vitro assays of a cell population's response to external factors, therefore an MTT assay was carried out to measure the effect of Liposome A on cell viability. The MTT assay measures the cell proliferation rate and conversely, when metabolic events lead to apoptosis or necrosis, the reduction in cell viability (balance between proliferation and cell death). This assay involves the reduction of tetrazolium salts by mitochondrial dehydrogenase enzymes. The yellow tetrazolium MTT (3-(4,5-dimethylthiazolyl-2)-2,5-diphenyltetrazolium bromide) is converted to the purple product Formazan, by metabolically active cells, through the action of dehydrogenase enzymes. The resulting intracellular purple formazan can be solubilised and quantified spectrophotometrically. In this manner, the viability of cells in the presence of the added gadolinium liposomes can be measured and quantitated.

Figure 12:
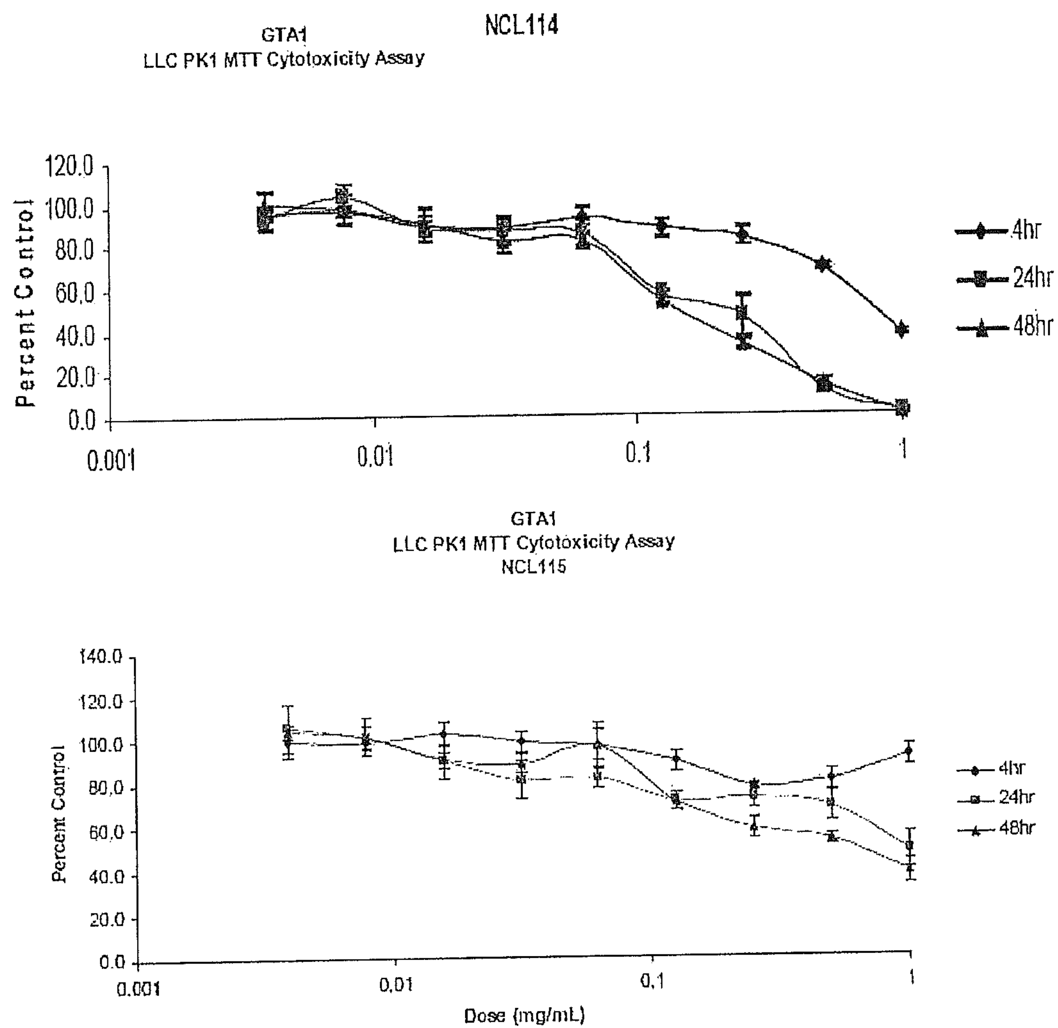
FIG. 12 shows the results of the MTT cell viability assay on kidney LCC PK1 cells using the Liposome A particles of the present invention at various doses and three incubation periods.

Two cell lines, LLC-PK1 kidney cells and Hep G2 liver cells were seeded at $2.5\times10^{-5}$ cells/mL in 96 welled plates and incubated in growth media for 24 h prior to assay. Then Liposome A was added to the cells at a concentration of 0.004-1.0 mg mL-1 and the cells incubated for 6, 24, and 48 h. The cytotoxicity was determined and the data are presented in FIG. 12.

The MTT viability assay on kidney LLC PK1 cells revealed a good level of cell viability, after the addition of the liposomes, and viability was shown to fall only at the higher dose and incubation periods. The toxicity of Liposome A is lower than the control nanoparticle, this effect is perhaps due to the carboxylic acids of the DOTA head group, which in the Liposome A formulation, are chelated to $Gd^{3+}$, and therefore become neutral and relatively inert within the cellular environment.

Figure 13:
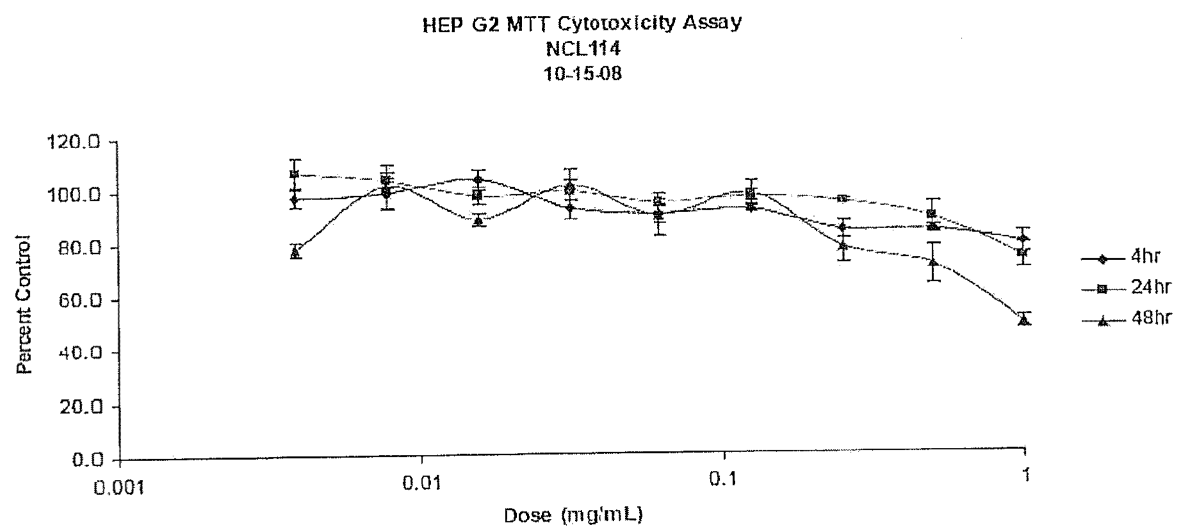
FIG. 13 shows the results of the MTT cell viability assay on HepG2 liver cells using the Lipsome A particles of the present invention at various doses and three incubation periods.
Figure 13:
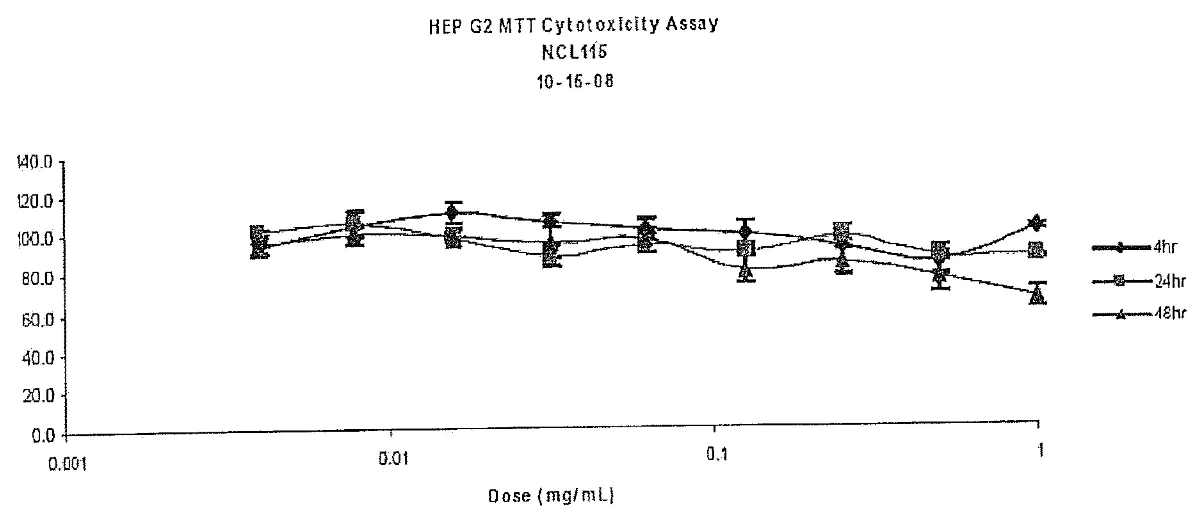

HepG2 cellular viability was minimally affected as a result of the addition of Liposome A or the control nanoparticle (FIG. 13). However, Liposome A toxicity was lower than the control nanoparticle, where cell viability reductions were observed at the higher dose and longer incubation periods (Top graph, FIG. 13).

Lactate Dehydrogenase (LDH) Cytotoxicity Assay

Figure 14:
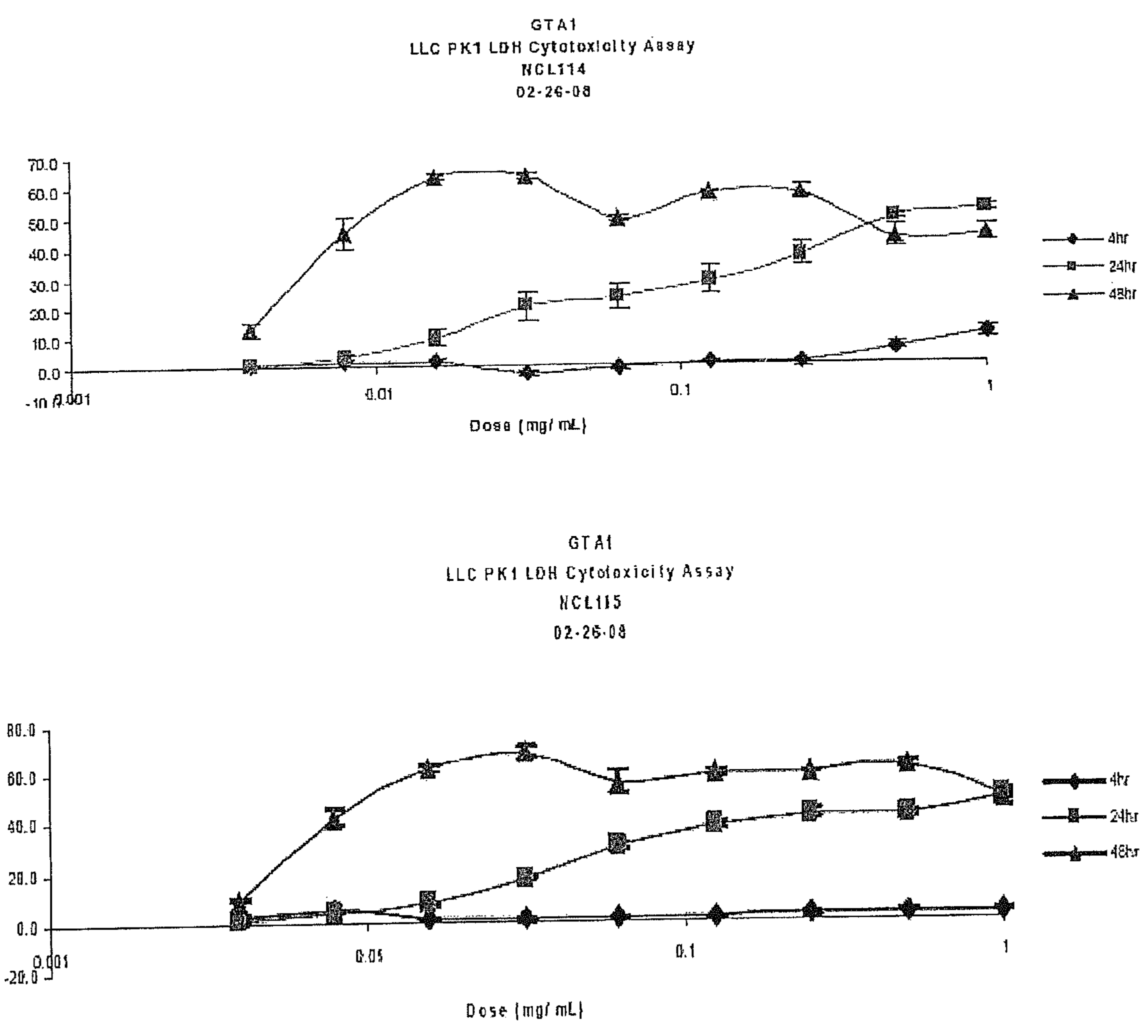
FIG. 14 shows the results obtained in the LDH assay of on kidney LCC PK1 cells using the Liposome A particles of the present invention at various doses and three incubation periods.

The LDH assay is a non-radioactive colourimetric cytotoxicity assay that quantitatively measures LDH, which is a stable cytosolic enzyme that is released upon cell lysis during cell death. The amount of LDH released in the cell media is measured with a 30-minute coupled enzymatic assay, which results in the conversion of a tetrazolium salt (INT) into a red formazan product. The amount of colour formed is proportional to the number of lysed and therefore dead cells. The results are then normalised against controls such as the LDH released from cells with no compounds added to them. FIG. 14 presents the NCL LDH assay results on kidney LLC PK1 cells for the control nanoparticle and Liposome A.

The data in FIG. 14 show cellular toxicity to be low at the lower dose range and incubation period (4 h). Liposome A appears less toxic when compared to the control nanoparticle.

Figure 15:
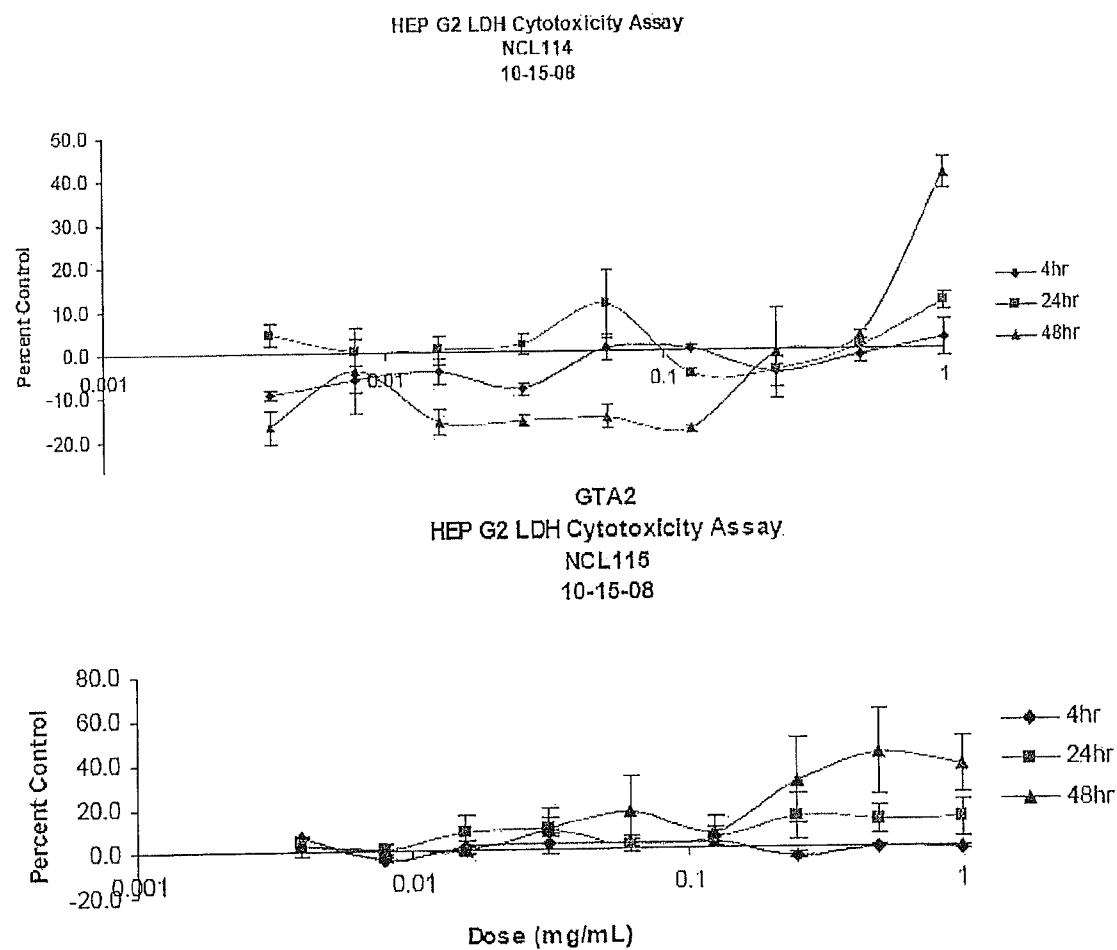
FIG. 15 shows the results obtained in the LDH assay on HepG2 liver cells using the Lipsome A particles of the present invention at various doses and three incubation periods.

Cytotoxicity of the control liposomes is more variable for the control nanoparticles, and it appears that these particles are more toxic to HepG2 liver cells (FIG. 15, top) than Liposome A. HepG2 toxicity and therefore the liver toxicity of Liposome A appear quite low at all concentrations and incubation periods. These data confirm an overall low toxicity for Liposome A.

In Vivo Tumour Imaging

Mouse tumours of human cancer are a good model for preliminary investigations of imaging agents and their effectiveness as tumour signal enhancers. The human ovarian cancer cell line IGROV-1 was used to induce tumours in Balb/c nude mice. Here, cells were injected under the right flanks of 6-8 week old female mice, and after two weeks the mice had grown large enough tumours suitable for imaging. Liposome A particles were prepared in HEPES buffer and injected through the tail vein of tumour bearing mice, a method that ensures rapid entry of the liposomes into the blood circulation. Prior to injection, baseline MRI scans were obtained on a 4.7 T magnet in order to identify the tumour and measure baseline signal intensity values. Post liposome injection, the mice were then imaged at 2 h, 16 h and 24 h post injection. $T_1$-weighted images for each time point were obtained and the percent signal intensity enhancement as a result of the accumulation of the liposomes within the tumour tissue was calculated from tumour signal intensity values generated from the tumour tissue (see FIG. 16).

Figure 16:
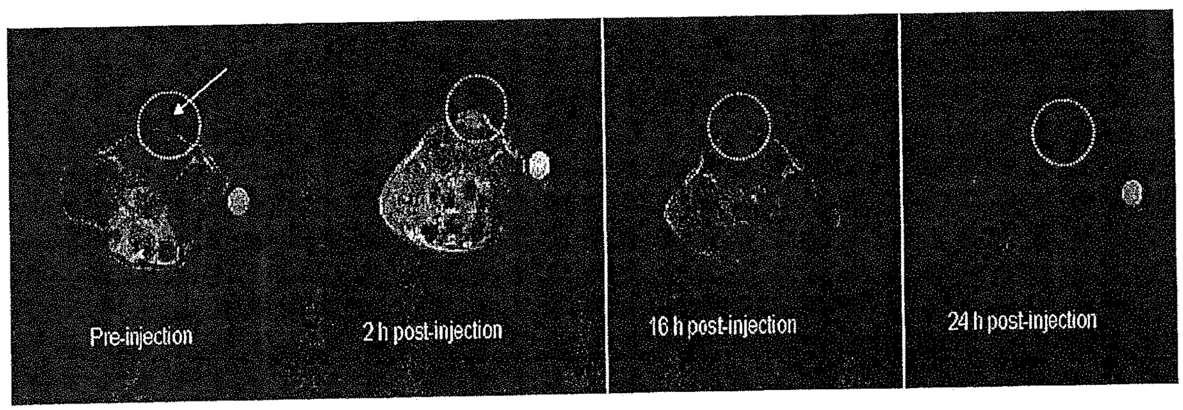
FIG. 16 presents magnetic resonance images of tumour bearing mice at various periods after injection with a preparation comprising Liposome A, with the dotted white circles marking the tumour area and the white arrow pointing to the tumour location.
Figure 17:
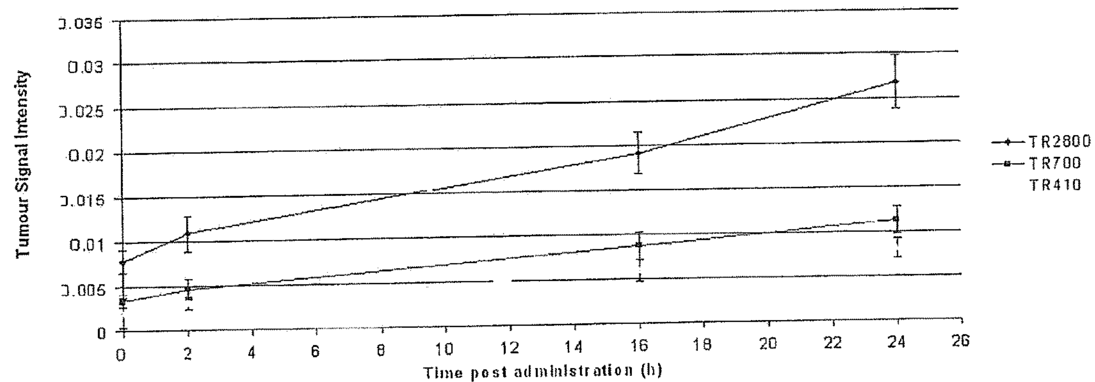
FIG. 17 shows a graph of % tumour signal intensity at various TR time points post administration of Liposome A over the 24 hour MRI experiment in which the images of FIG. 16 were obtained.

FIG. 16 presents MR images of tumour bearing mice, the tumour appears dark prior to injection of Liposome A, and becomes more enhanced post-administration of the liposomes. This effect is persistent up to the 24 h end point of the experiment. The tumour signal enhancement of Liposome A is further confirmed by FIG. 17, where at different TR time points the tumour signal intensity is seen to rise consistently over time, confirming the gradual accumulation of Liposome A in the tumour due to the EPR effect.

Figure 18:
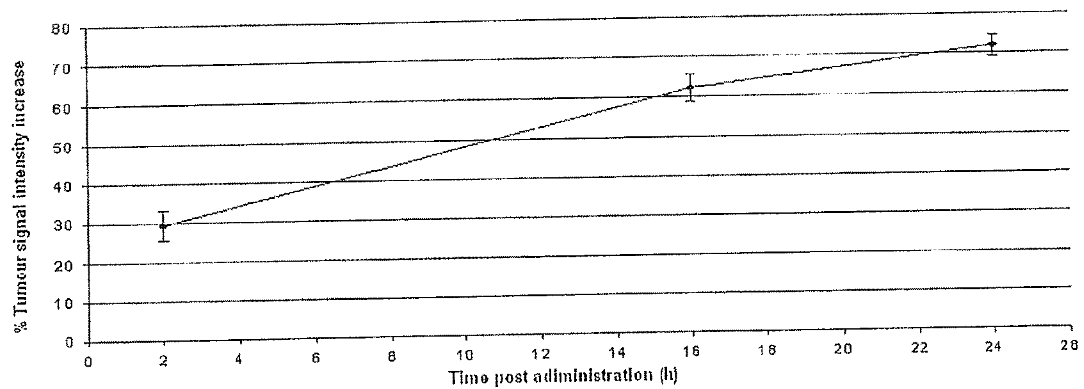
FIG. 18 shows a graph of tumour signal intensity increase over time, post-administration of Liposome A over the 24 hour MRI experiment in which the images of FIG. 16 were obtained.

When this data is represented as tumour signal intensity increase in FIG. 18, we can see that the tumour signal intensity increases over 24 h, and a 72% signal increase is achieved up to the 24 h end point of the experiment. This data is very impressive and demonstrates the utility of Liposome A according to the present invention as a "passively" targeted tumour imaging agent.

At 24 h post injection, the mice were sacrificed and their tumours excised. The tumours were frozen, fixed and subjected to cryo-sectioning, where 7 m sections were cut and the slides analysed for their fluorescence using microscopy. The inclusion of the red fluorescent lipid DOPE-Rhodamine in the Liposome A formulation allowed for the bimodal assessment of liposome localisation within the tumour tissue.

Figure 19:
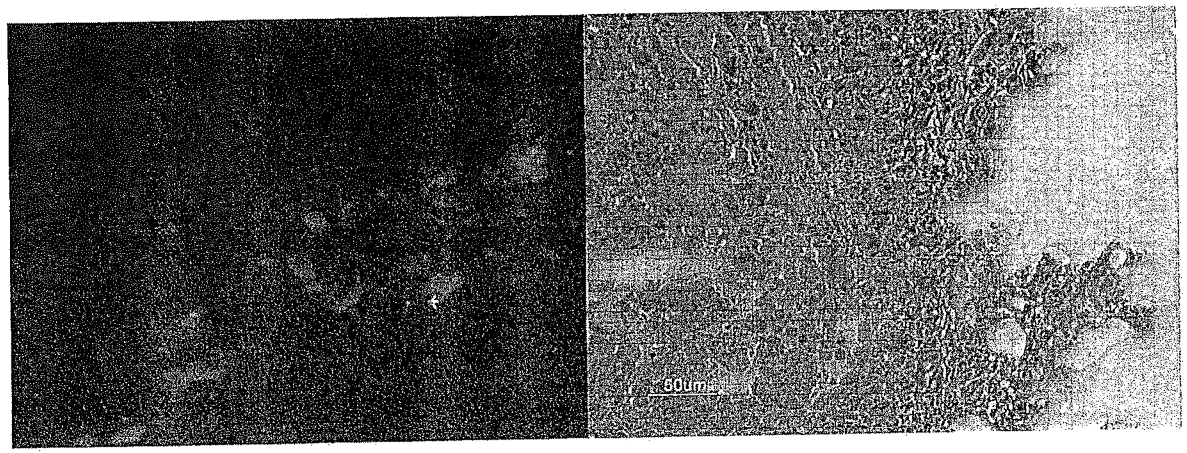
FIG. 19 shows the results of fluorescence microscopy on sectioned IGROV-1 tumours post Liposome A administration; in the left panel a fluorescence image is shown while in the right panel an H&E stain (×400) is depicted)

As expected in view of the MRI studies, histological analysis of the tumour sections revealed a very high level of fluorescence signal in the tumour tissue (see FIG. 19). The appearance of hyper fluorescence signals within the tumour tissue was observable. These fluorescence intensity results provided qualitative visual congruence with the MR images and validated the accumulation of Liposome A within the xenograft tumours. Tumour tissue has microvessels with large fenestrations and as such the liposomes are able to extravasate into the tumour. These extravasated liposomes are not cleared due to an impaired lymphatic drainage system and may accumulate within the tumour extracellular fluid over time.

Conclusion

Liposome A is a novel liposome nanoparticle formulation that is capable of effective tumour imaging by MRI. The incorporation of DSPC, a fully saturated phospholipid for use in the Gd.DOTA.DSA liposomes of the present invention gives excellent results. The results demonstrate clearly that Liposome A has low liver toxicity and a very high MRI signal enhancement activity. This is believed to be due to the optimal size of Liposome A, a typical Gd.DOTA.DSA liposome of the present invention, as it is small enough to be accumulated in the tumour due to the EPR effect and this smaller size also prevents it being accumulated in the liver in particular due to the reduction of Kupffer cell uptake.

Example 2 Liposome B

In a further experiment, we developed a further tumour targeted MRI active liposome referred to hereafter as Liposome B.

Figure 20:
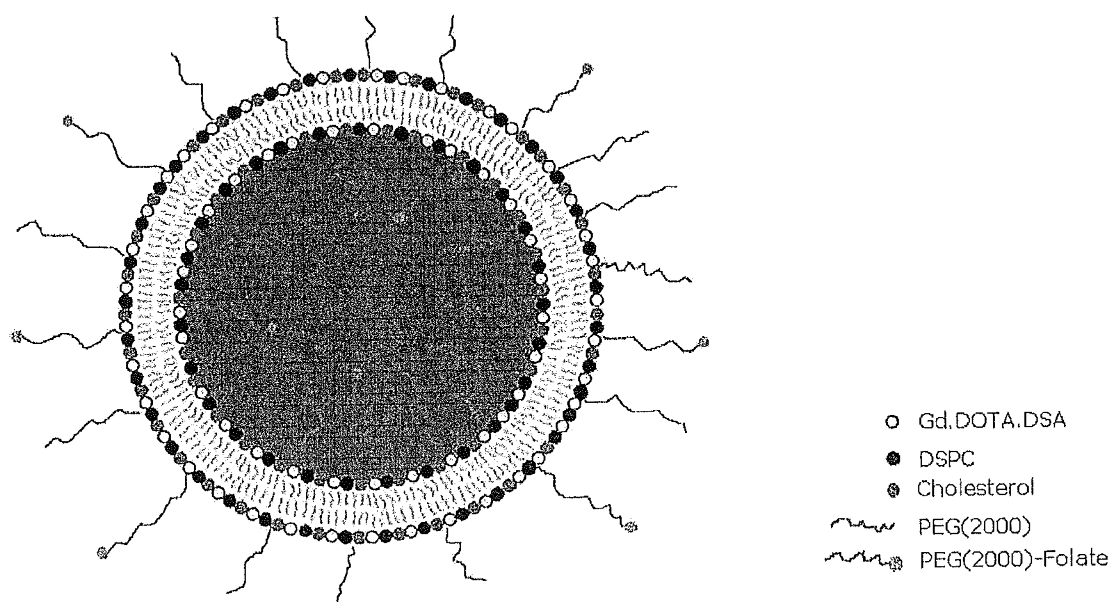
FIG. 20 provides a depiction of one of the preferred liposomes of the invention, liposome B, a novel MRI active liposome which has a folate receptor moiety and which has tumour imaging utility.
Figure 21:
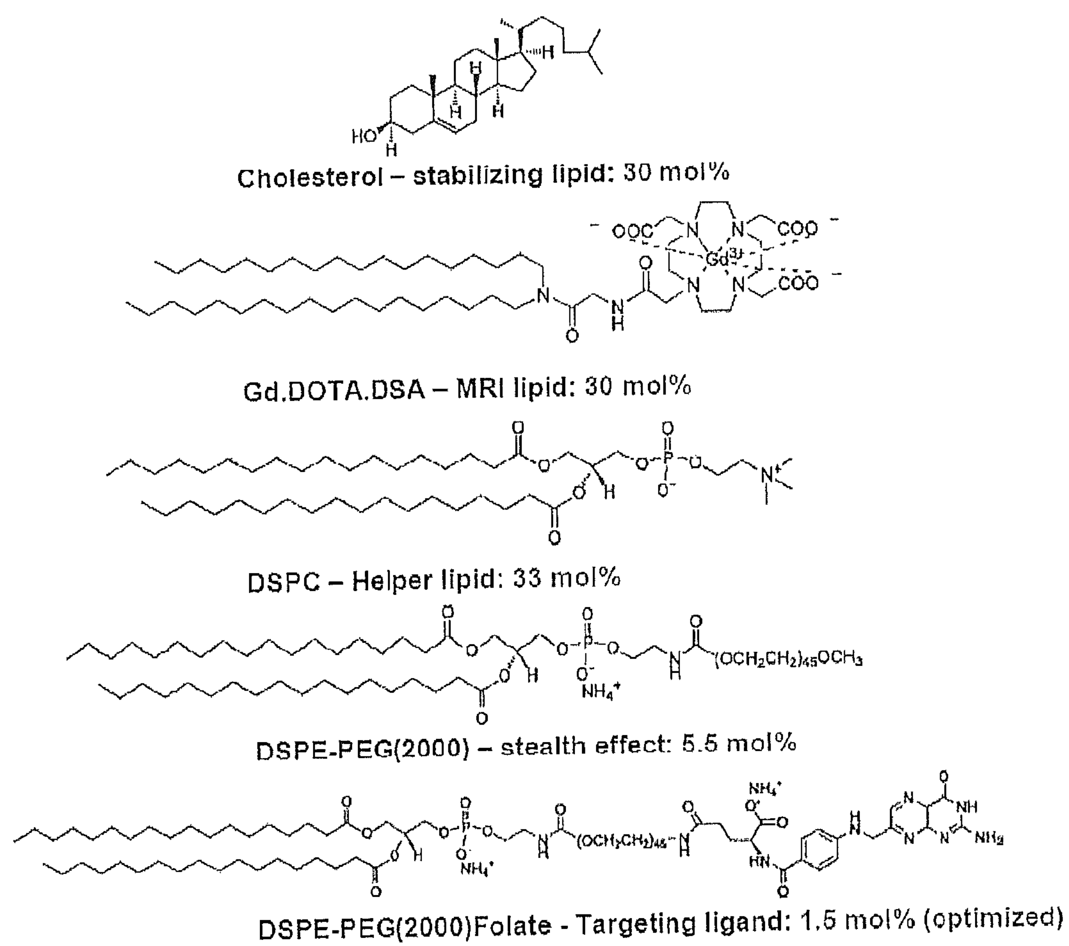
FIG. 21 depicts the structures of lipids forming one of the preferred liposomes of the invention, liposome B.

Liposome B is a novel tumour targeted liposome nanoparticle for MRI. As part of our targeted-liposome research investigations, we developed the folate-targeted paramagnetic liposome, Liposome B (see the depiction of Liposome B in FIG. 20) which showed enhanced accumulation in a folate-receptor expressing tumour model. The particles were formulated to ensure a size distribution of approximately 100 nm with a low polydispersity index. IGROV-1 cells were used to induce tumours in nude Balb/c mice and the folate-targeted liposomes were injected intravenously. Rapid accumulation of the folate-targeted liposomes within the tumour tissue compared to non-targeted liposomes was observed. The formulation for Liposome B is similar to Liposome A, with the exception that the molar percentage of the DSPE-PEG2000 stealth lipid is reduced by 1.5 mol % in order to incorporate the targeting amphiphile: DSPE-PEG-2000(Folate) [distearoylphosphatidylethanolamine-polyethylene glycol (2000)-folate] (see FIG. 21 for particle composition).

The human nasopharyngeal KB carcinoma cell line is considered to have the highest level of FR expression, yet the number of cases for this cancer are low in comparison to ovarian cancer which has the highest frequency (>90% of cases).[27] In particular, the α-FR isoform which is a glycosyl phosphatidylinositol (GPI-anchored membrane protein is highly expressed in ovarian carcinoma.[28] Additionally, the α-FR isoform has also been shown to have specific biomarker value, aiding in the identification of metastatic tumour site origin.[29] Therefore, we were interested in using this receptor in order to test the efficacy of folate targeted bimodal liposomes for the imaging of ovarian tumours using MRI. Folate-based liposomal drug delivery has been studied extensively,[30] however, the rate-enhancing effect of liposome accumulation in tumours due to folate targeting has not been studied dynamically in real-time to a great extent. Effective tumour signal enhancement was anticipated since the FR is expressed in significantly lower amounts in normal tissue, limited mainly to kidney tubuli, lung epithelium, and placenta tissue.[31] To asses the value of the addition of a targeting ligand on the rate and extent of accumulation of liposomes in solid tumours, FR targeted bimodal fluorescent and paramagnetic liposomes were formulated and compared to non-targeted liposomes by both MRI and fluorescence microscopy.

Figure 22:
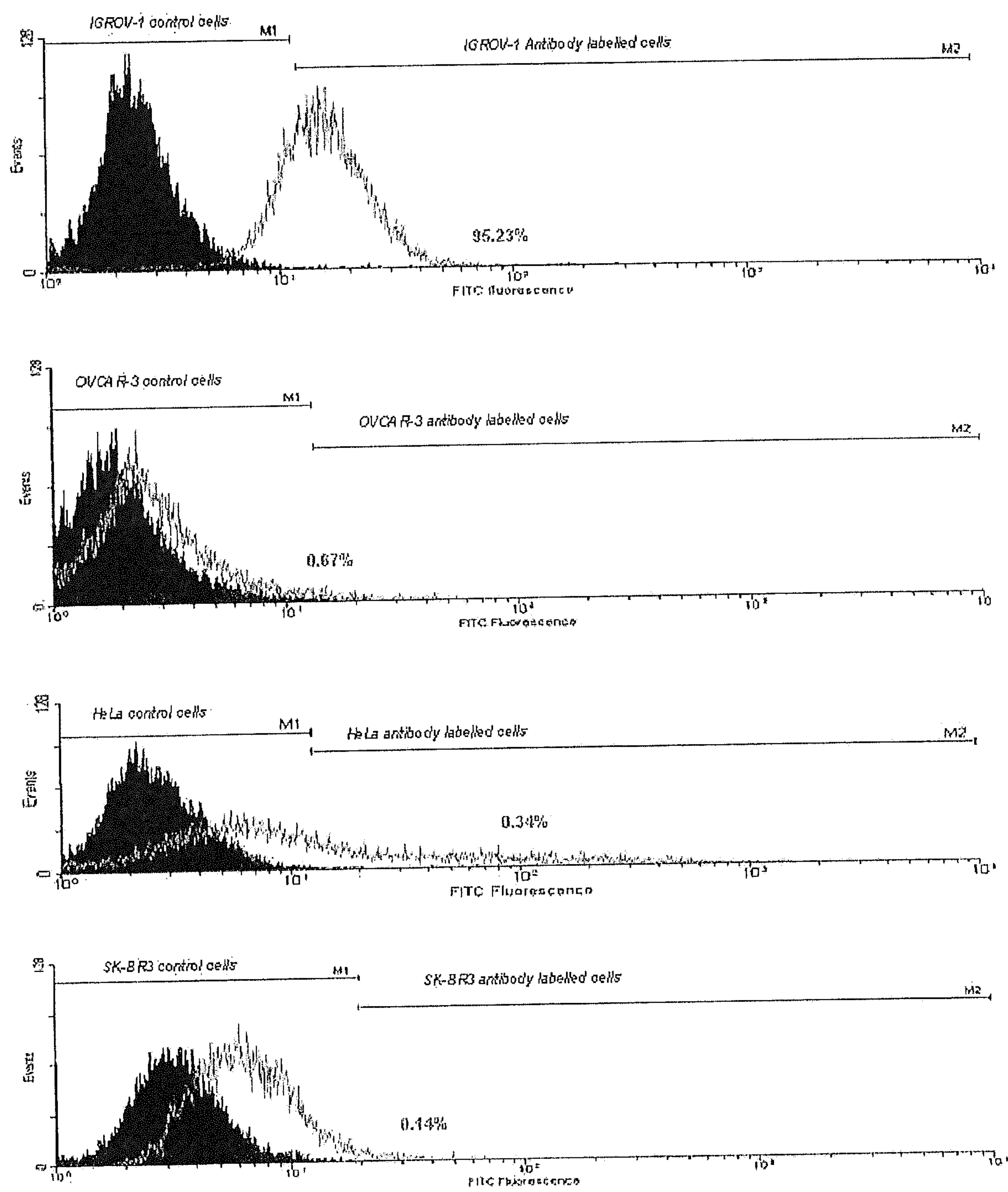
FIG. 22 shows the results of FACS analysis of four cell lines for α-FR expression.

In order to establish whether the IGROV-1 cell line, a human ovarian carcinoma cell line expresses a sufficient level of the folate receptor, FACS analysis of four different cell lines was carried out. For this purposes, the α-folate receptor (α-FR) isoform which is a folate transporter with restricted expression levels in normal tissues was chosen. To measure the α-FR expression levels of the human ovarian cell lines IGROV-1, OVCAR-3 and HeLa (cervical cancer) cells, flow cytometry experiments were carried out. In addition to these cell lines a breast cancer cell line (SKBR-3) was also analyzed as a negative control cell line with no α-FR expression. Cells were grown in folic acid free media and incubated with serum to block any non-specific interactions. Immunostaining was carried out with a monoclonal antibody (MAb Mov18/ZEL) specific for the α-FR, and post incubation with this antibody, a secondary FITC labelled antibody (Goat anti-body IgG, FITC conjugated) was allowed to incubate with the cells. Post staining, the cells were fixed and analyzed by fluorescence microscopy. From the FACS α-FR expression analysis (see FIG. 22), where all cell lines were cultured under the same standardized conditions using folate free cell culture medium, it was shown that the IGROV-1 cell line exhibited a distinctly higher level of α-FR expression. From these typical FACS data the α-FR expression was measured to be in the order: IGROV-1>>OVCAR-3>HeLa>SKBR-3 (three days post-seeding).

Having established the over-expression of the α-FR on the IGROV-1 cell line, Liposome B targeted liposomes were prepared for specific cell receptor binding and uptake into IGROV-1 tumour cancer cells.

The percentage of the folate targeting amphiphile was initially optimized prior to MR imaging. Table 3 shows a series of liposomes with varying folate amphiphile formulated for incubation with IGROV-1 cells.

TABLE 3

Formulation of Liposome BTM with varying mol % of DSPE-PEG2000 targeting lipid.
Liposomes used in folate ligand optimization experiments

| Gd.DOTA.DSA (mol %) | DSPC (mol %) | Chol (mol %) | DSPE-PEG2000 (mol %) | DSPE-PEG2000 (folate) (mol %) | Size (nm) | PI |
|---|---|---|---|---|---|---|
| 30 | 33 | 30 | 6.99 | 0.01 | 134.33 ± 9.07 | 0.401 ± 0.207 |
| 30 | 33 | 30 | 6.97 | 0.03 | 112.36 ± 3.164 | 0.266 ± 0.094 |
| 30 | 33 | 30 | 6.5 | 0.5 | 103.46 ± 12.70 | 0.377 ± 0.337 |
| 30 | 33 | 30 | 5.5 | 1.5 | 146.3 ± 3.897 | 0.602 ± 0.141 |
| 30 | 33 | 30 | 4 | 3 | 84.766 ± 9.729 | 0.960 ± 0.487 |
| 30 | 33 | 30 | 7 | 0 | 79.3 ± 1.997 | 0.424 ± 0.186 |

Figure 23:
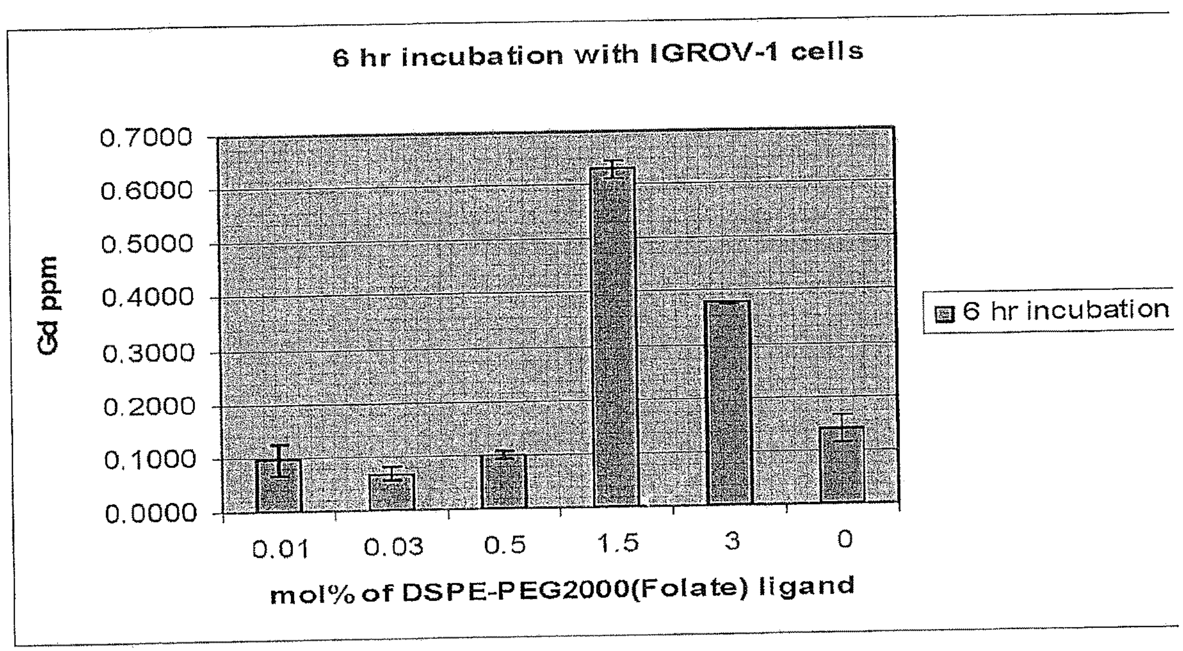
FIG. 23 is a graph setting out the amount of Gd taken up by IGROV-1 cells post incubation with Liposome B with varying mol % of the folate targeting lipid.

For the ligand optimization experiments, Liposome B liposomes shown in Table 3 were added to IGROV-1 cells in culture and incubated for 6 h. After this incubation period, the cells were washed, lysed and subjected to ICP-MS measurements for their $^{157}$Gd content. FIG. 23 presents the obtained data. From this data we can see that the liposome formulation with the highest uptake into IGROV-1 cells is the one containing 1.5 mol % of DSPE-PEG-2000(Folate). Our previous published work utilized neutral PEGylated liposomes that incorporated DOPC, and a 3 mol % of the DSPE-PEG-2000(Folate) targeting ligand, however, Liposome B requires half as much targeting ligand, which reduces the production costs drastically. Thus, it can be seen this reduction in cost owing to the need for only half the amount of targeting ligand represents a further advantage provided by the use of fully saturated phospholipids such as DSPC in the liposomes of the present invention.

Liposome B is a novel formulation that incorporates an optimized ratio of the targeting ligands, established using the same cell line from which tumours were grown for in vivo MR imaging experiments.

Figure 24:
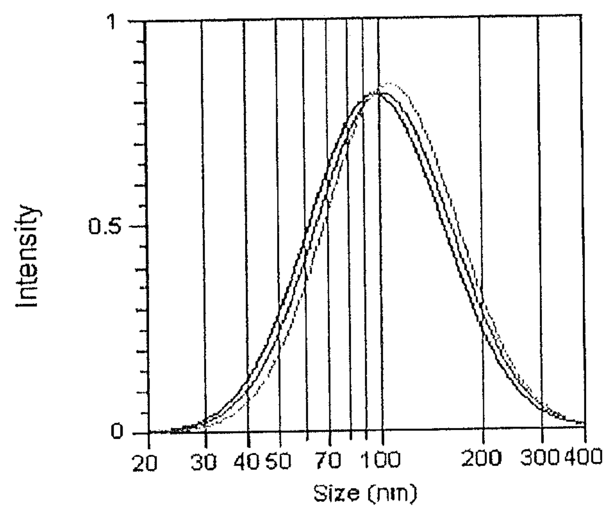
FIG. 24 presents data on the size and polydispersity distributions of Liposome B.

Having optimized the targeting ligand ratio of Liposome B liposomes, the liposomes were then characterized for their size and distribution. FIG. 24 presents data on the size characterization of Liposome B particles. The particles have an average size of approximately 100 nm, with the filtered particles having an excellent polydispersity index.

In Vitro Toxicity

Figure 25:
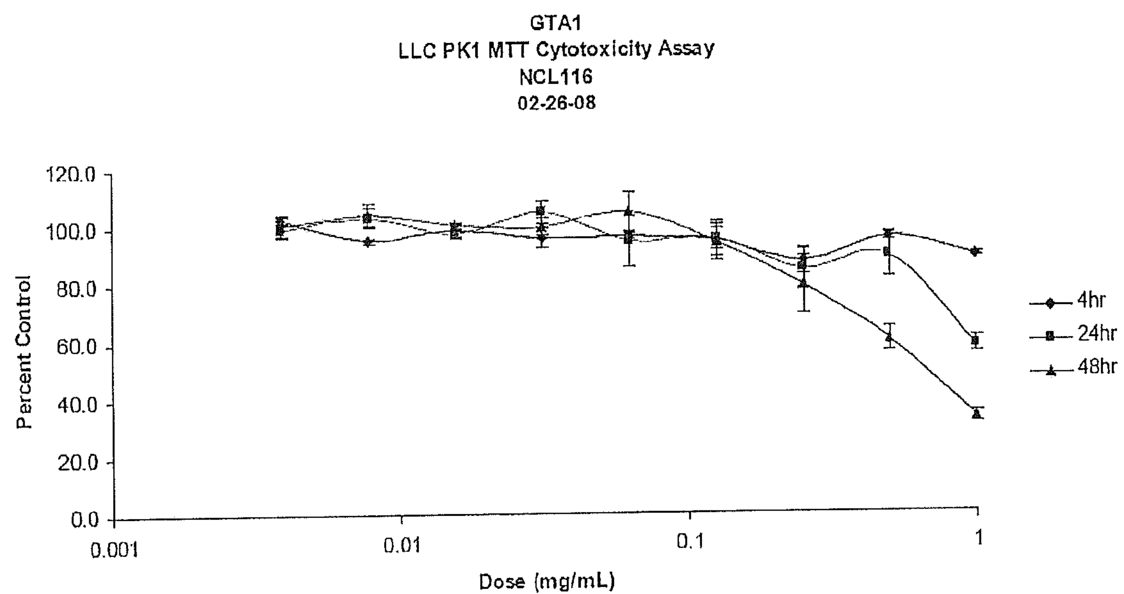
FIG. 25 is a graph showing the results of a MTT assay with Liposome B particles at various doses and three incubation periods in LCC PK1 cells.
Figure 26:
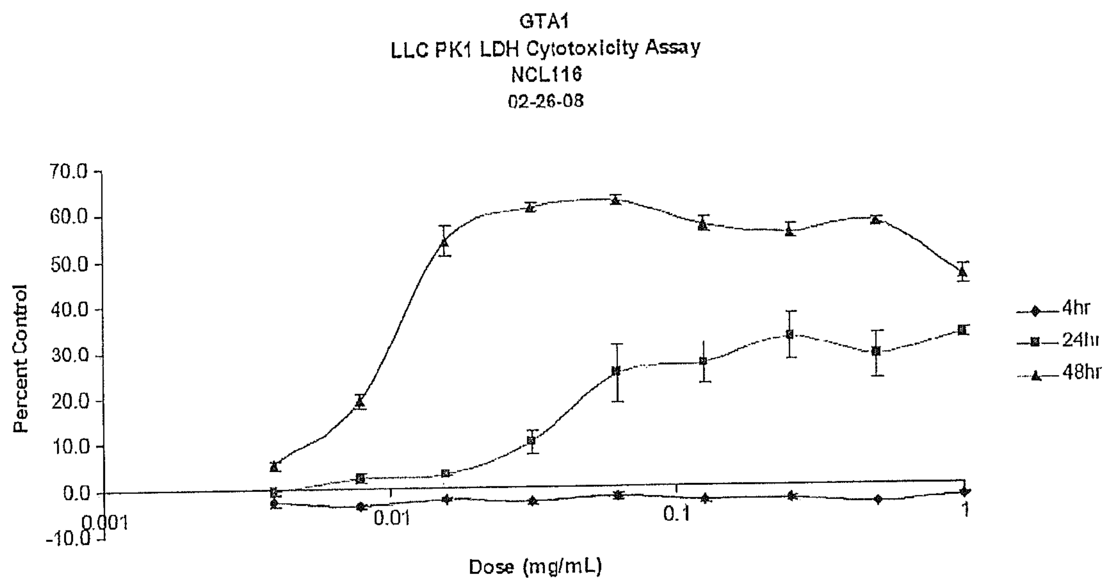
FIG. 26 is a graph showing the results of an LDH cytotoxicity assay with Liposome B particles at various doses and three incubation periods in LCC PK1 cells.

MTT assays on LLC PK1 kidney cells were performed on Liposome B liposomes and cell viability was not affected to a great degree at the majority of doses and incubation times (see FIG. 25). The higher dose and incubation period did lead to a reduction in cellular viability, indicating the optimal dose range to be between 0.001 and 0.5 mg/mL. The LDH assay data are presented in FIG. 26, the toxicity effects of Liposome B here appear to become much more pronounced at the 48 h incubation period.

Relaxivity of Liposome B Liposomes

The relaxivity of Liposome B liposomes was measured by formulating liposomes with varying concentrations of the Gd.DOTA.DSA lipid to obtain 5 formulations with atomic Gd concentrations within the range 1.972 to 0.2466 mM. The relaxivities of Liposome B and folate targeted liposomes containing DOPC lipid (as per our previous publication (Bioconjugate Chem. 2009, 20, 648-655) are shown in Table 4. As the MRI active Gd lipid: Gd.DOTA.DSA and its concentration is the same in both formulations, the $r_1$ and $r_2$ relaxivities obtained at 4.7 T are comparable.

TABLE 4

Relaxivity comparison of Liposome B liposomes with DSPC and Folate targeted DOPC containing liposomes.

| DOPC | | DSPC | |
|---|---|---|---|
| $r_1$ | 1.3006 | $r_1$ | 0.9126 |
| $r_2$ | 5.3794 | $r_2$ | 5.555 |

In Vivo Tumour MRI

Figure 27:
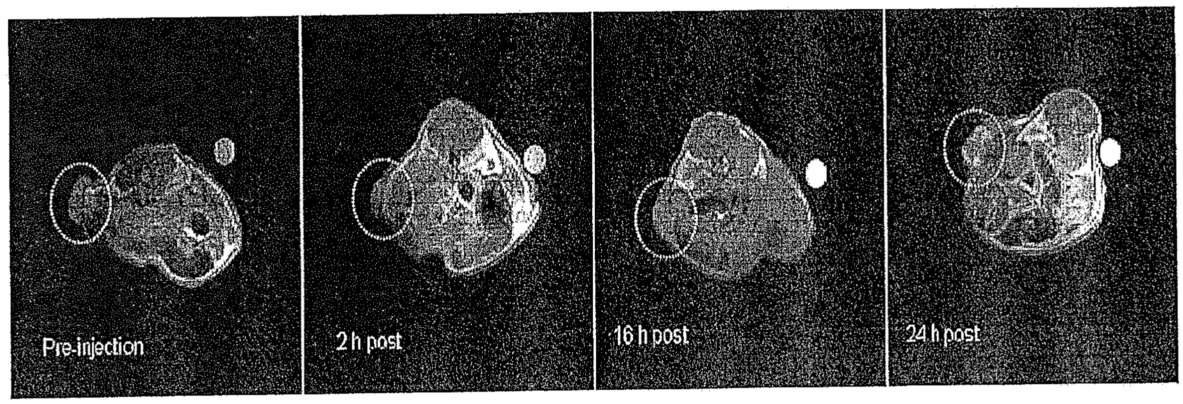
FIG. 27 presents magnetic resonance images of tumour bearing mice at various periods after injection with a preparation comprising Liposome B, with dotted white circles marking the tumour location.

Liposome B particles (total liposome concentration; 15 mg $mL^{-1}$) were prepared in HEPES buffer (20 mM, NaCl, 135 mM, pH 6.5) and injected through the tail vein of IGROV-1 tumour bearing mice. Prior to injection, baseline MRI scans were obtained on a 4.7 T magnet in order to identify the tumour and measure $T_1$ baseline values. The mice were then imaged at 2 h, 16 h and 24 h intervals post injection. Percent signal enhancement as a result of the accumulation of the Liposome B particles within the tumour tissue was calculated from signal intensities generated from the tumours. FIG. 27 presents the MR images of tumours at pre-injection, 2, 16 and 24 h post administration of Liposome B. The tumour images reveal a bright rim of enhanced signal around the tumour area at the 24 h time point, showing the great effectiveness of the folate receptor targeted paramagnetic Liposome B according to the present invention.

Figure 28:
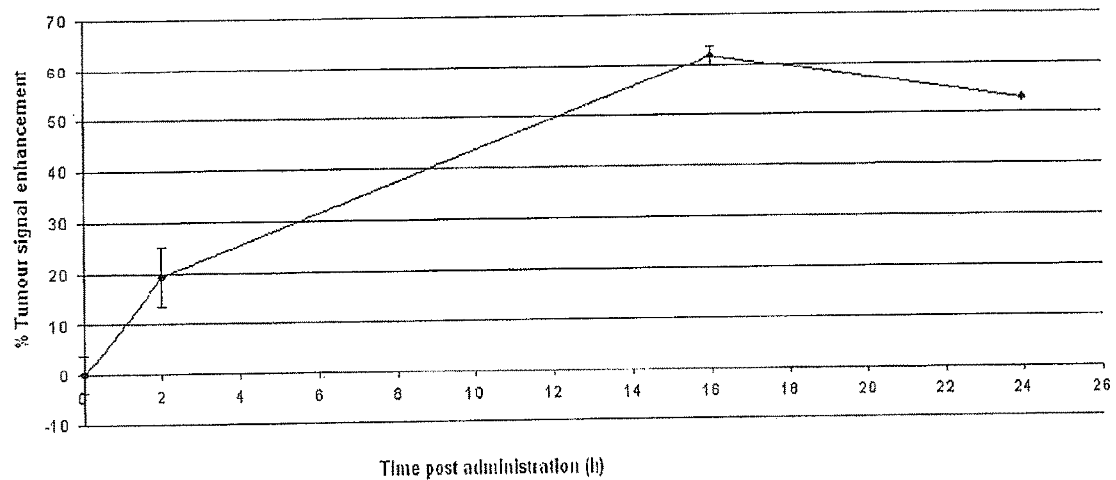
FIG. 28 shows a graph of % tumour signal intensity at various TR time points post administration of Liposome B over the 24 hour MRI experiment in which the images of FIG. 27 were obtained (n=3)

The measured tumour signal intensity values (see FIG. 28) show that within just 2 h post i.v. injection the active and specific targeting effect of the folate liposomes is apparent where the tumour signal is enhanced by 20%. The signal enhancement is then continually increased up to the 16 h imaging time point, where a 62% tumour signal enhancement is achieved. This substantial enhancement is observed despite injection of Liposome B particles which contain half the amount of Folate targeting ligand as compared to previous DOPC-3 mol % DSPE-PEG2000 (Folate) containing liposomes.

Further novelty and utility of Liposome B is demonstrated from the fact that after the 16 h peak in tumour signal intensities, the tumour signal starts to drop. Although with Liposome A tumour signal intensity increases up to the 24 end-point, this decreasing tumour signal intensity effect of Liposome B is advantageous as the particles are "naturally" cleared from the tumours, post imaging, which is a requirement of any safe and biocompatible nanoparticle. Although faster accumulation rates and doses at tumour sites can be achieved using targeting ligands, recent reports have drawn attention to the safety of prolonged accumulation and retention of targeted nanoparticles. We believe that Liposome B is an optimal MRI active liposomal nanoparticle which within the μM dose range can enhance tumour tissue substantially, clear after the signal enhancement saturation point, and demonstrates advantages over current clinically available small molecular weight MRI contrast agents.

Histology of IGROV-1 Tumours

Figure 29:
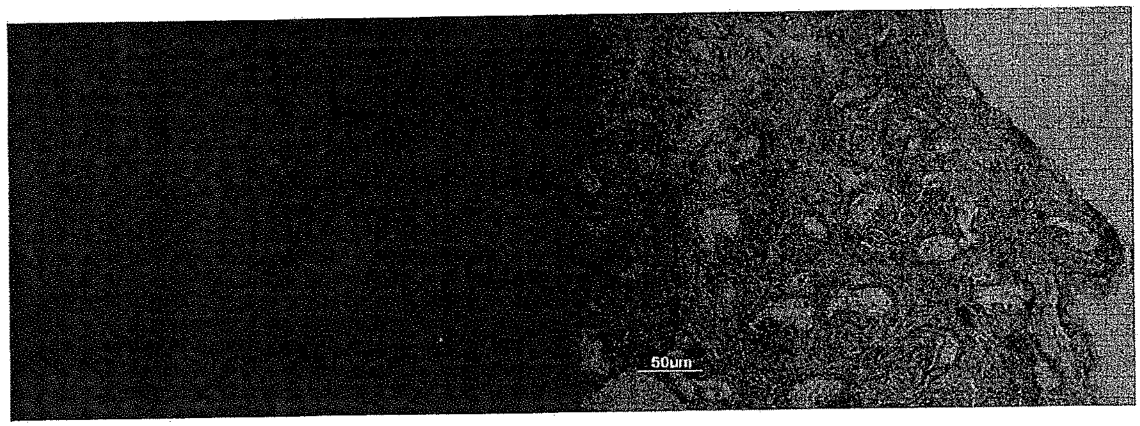
FIG. 29 shows the results of fluorescence microscopy on sectioned IGROV-1 tumours post Liposome B administration; in the left panel a fluorescence image is shown while in the right panel an H&E stain (X 400) is depicted)

Following MRI, the mice were then sacrificed and the tumours excised, frozen, fixed and sectioned for histological analysis. The inclusion of the fluorescent DOPE-Rhodamine lipid in the liposome formulation allows for post-mortem analysis by fluorescence microscopy which is a sensitive indication for the presence of liposomes within the tumour tissue. FIG. 29 presents fluorescence microscopy images of sectioned tumours 24 h post Liposome B injection. The presence of intense red fluorescence from these sectioned tumour slices is indicative of the accumulation of the targeted B Liposomes in the tumour tissue.

These findings suggest that folate targeting for the in vivo imaging of tumours presents a robust and broad platform for tumour imaging.

Conclusions

In the quest for ever more optimal nanoparticles for the effective imaging of solid tumours, considerations of particle size, charge and targeting elements are key requirements for successful particle development for tumour imaging. The results of Experiments 1 and 2 conclusively show that the novel liposomes of the present invention demonstrate optimal properties that make them particularly suitable for use as contrast agents in magnetic resonance imaging of tumours.

Experimental

Materials

Phosphatidylethanolamine-lissamine rhodamine B (DOPE-Rhodamine), Cholesterol, distearoylphospocholine (DSPC) and 1,2-Distearoyl-sn-Glycero-3-Phospocholine-N-Methoxy(Polyethylene glycol)-2000 (DSPE-PEG2000) were purchased from Avanti Polar Lipids Inc. (Alabaster, Ala., USA). All other chemicals were of analytical grade or the best grade available and purchased from Sigma-Aldrich (UK) or Macrocyclics (USA). Gd.DOTA.DSA was synthesised as follows.

General Procedures $^1$H NMR spectra were recorded on a 400 MHz Bruker Advance 400 spectrometer. Chemical shifts are reported in parts per million (ppm) downfield from TMS, using residual chloroform (7.27 ppm) as an integral standard. Data are supported as follows: chemical shift, s=singlet, br=broad singlet, d=doublet, t=triplet, q=quartet, m=multiplet, coupling constants J are given in hertz (Hz). $^{13}$C NMR spectra were recorded on a 400 MHz Bruker Advance 400 spectrometer. Chemical shifts are reported in parts per million (ppm) downfield from TMS, using the middle resonance of $CDCl_3$ (77.0 ppm) as an integral standard. Infrared (IR) spectra were recorded on a JASCO FT/IR-620 infra-red spectrophotometer; absorption's are recorded in wavenumbers (vmax in $cm^{-1}$). Analytical HPLC was conducted on a Hitachi-LaChrom L-7150 pump system equipped with a Polymer Laboratories PL-ELS 1000 evaporative light scattering detector. HPLC gradient mixes assigned as follows: gradient mix A=$H_2O$/0.1% TFA; mix B=MeCN/0.1% TFA; mix C=MeOH. Mass spectra were performed using VG-070B, Joel SX-102 or Bruker Esquire 3000 ESI instruments. Melting points were determined on a Stuart Scientific SMP3 apparatus and are reported without correction. Reactions with air sensitive material were carried out by standard syringe techniques. $CH_2Cl_2$ was distilled over $P_2O_5$. Thin layer chromatographic (TLC) analyses were performed on Merck 0.2 mm aluminium-backed silica gel 60 F254 plates and components were visualised by illumination with UV light or by staining with potassium permanganate, acidic ammonium molybdate (IV), iodine, ninhydrin, Rhodamine B, dilute aqueous sulphuric acid or bromocresol green, where appropriate a Pharmacia LKB—Ultrospec III (deuterium lamp at 300 nm) was used to visualise the UV absorbance. Flash column chromatography was performed using Merck 0.040 to 0.063 mm, 230 to 400 mesh silica gel. Microscopy experiments were conducted on a Nickon Eclipse E600 microscope. FACS analysis was conducted on a Becton Dickinson FACSCalibur machine. All MRI experiments were conducted on a 4.7 T Magnex magnet (Oxford, UK) Varian Unity Inova console (Palo Alto, Calif., USA).

All procedures on animals were conducted in accordance with UK Home Office regulations and the Guidance for the Operation of Animals (Scientific Procedures) Act (1986).

Scheme 1 presents the synthetic route undertaken to produce the only in-house synthesised component of the liposomal nanoparticles put forward: Gd.DOTA.DSA lipid 4. This lipid is produced with ~98% purity as assessed by analytical HPLC.

Scheme 1.

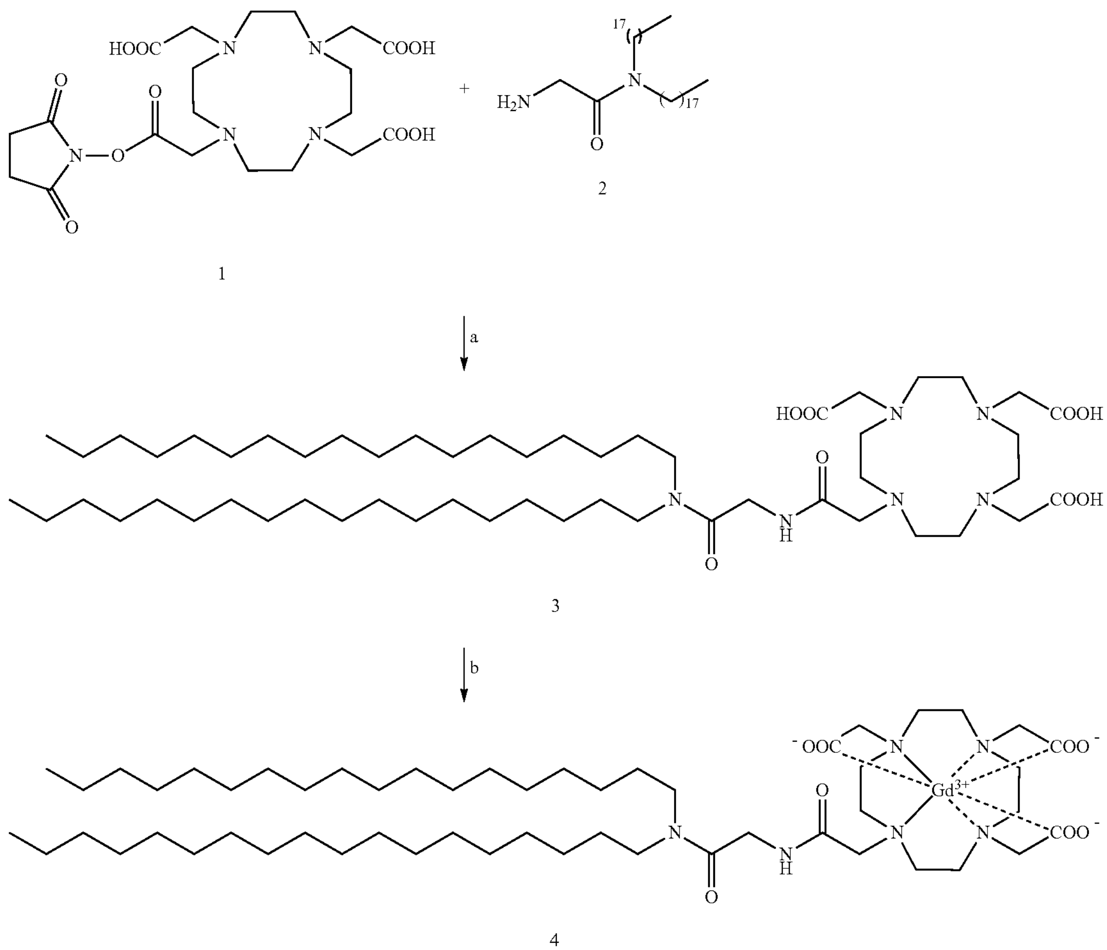

a: 3 eq. $Et_3N$, dry $CH_2Cl_2$, 45° C., 12 h, 68%. b: 6 $H_2O$•$GdCl_3$, $H_2O$, 90° C., 12 h quantitative.

Chemical Synthesis:

(i) 2-{4,7-Bis-Carboxymethyl-10-[(N,N-distearylamidomethyl-N'-Amidomethyl]-1,4,7,10-Tetra-Azacyclododec-1-yl}-Acetic Acid (DOTA.DSA) (3)

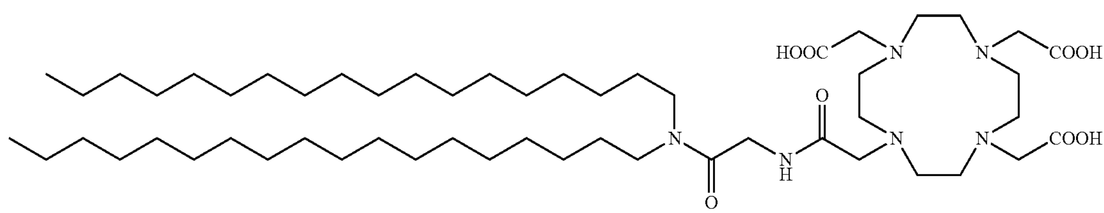 [SMILES: CCCCCCCCCCCCCCCCCCN(CCCCCCCCCCCCCCCCCC)C(=O)CNC(=O)CN1CCN(CC(=O)O)CCN(CC(=O)O)CCN(CC(=O)O)CC1]

DOTA-NHS-ester (100 mg, 0.120 mmol) and bis(steroylamide) (80.17 mg 0.139 mmol) were added to an evacuated flask, to which was added anhydrous $CH_2Cl_2$ (40 ml). Triethylamine (66.90 l, 0.480 mmol) was then added and the reaction stirred overnight under an atmosphere of $N_2$. The solvents were removed in vacuo and the crude mixture was purified by flash column chromatography (eluted with ($CH_2Cl_2$: MeOH: NH3 34.5: 9: 1): $CH_2Cl_2$ 1:9→9:1, v/v) to yield a white solid. Rf [$CH_2Cl_2$: MeOH: $H_2O$: 34.5: 9: 1 v/v] 0.61. $^1$H NMR (400 MHz, $CDCl_3$: MeOD: AcOD: 3: 1, 300K) δH (ppm) 10.55 (3H, s, br, 3×COOH), 5.30 (1H, s, br, $CH_2NHCOO$), 3.65 (6H, m, 3×$NCH_2COOH$), 3.22 (6H, m, 2×$NCH_2CH_2$, 1×$NCH_2CONH$), 2.58 (16H, s, br, 4×$NCH_2CH_2N$), 2.29 (2H, s, br , $CH_2NH$), 1.67-1.59 (4H, m, $OCNCH_2CH_2$), 1.46 -1.44(27H, d of s, J 6.0, $C(CH_3)3$× 3),1.25 (60H, s, chain $CH_2$'s), 0.90 (6H, t, J 6.8, $CH_{3×2}$). FTIR: vmax (nujol)/$cm^{-1}$ 3750.56, 2726.56, 1889.87, 1793.63, 1681.21, 1534.22. HPLC: tR=34.16 min, column C-4 peptide, gradient mix: 0.0 min [100% A], 15-25.0 min [100% B], 25.1-45.0 min [100% C], 45.1-55.0 min [100% A]; flow: 1 mL/min. HRMS (FAB+) calculated for 54H104N608 m/z 964.7916, found 987.7833 $(M+Na)^+$.

(ii) Gadolinium (III) 2-{4,7-Bis-Carboxymethyl-10-[(N, N-Distearylamidomethyl-N'-Amido-Methyl]-1,4,7,10-Tetra-Azacyclododec-1-yl}-Acetic Acid (Gd.DOTA.DSA) (4)

Boc-glycine (310 mg, 1.77 mmol) and dioctadecylamine (923.96 mg, 1.77 mmol) were dissolved in dry chloroform (30 ml). HBTU (2-(1H-Benzotriazole-1-yl)-1,1,3,3-tetramethyluronium hexafluorophosphate) (804.12 mg, 2.12 mmol) and DMAP (4-dimethylaminopyridine) (648.72 mg, 5.31 mmol) were added to the solution and the reaction was stirred at room temperature under $N_2$ for 12 h. The solvents were removed in vacuo. The mixture was dissolved in $CH_2Cl_2$ (50 mL) and extracted with $H_{2O}$ (3×50 mL). The combined aqueous extracts were back extracted with 2: 1 $CH_2Cl_2$: MeOH (2×50 mL), the solvents reduced and re-dissolved in diethyl ether and a subsequent extraction with 7% citric acid and $H_2O$ was performed; the organic layer was washed with brine, collected and filtered through celite and finally dried over $MgSO_4$. The diethyl ether was evaporated in vacuo to yield a pure white solid (1.164g, 97% yield, mp=82-85° C.). Rf [$CH_2Cl_2$: MeOH: $H_2O$:

34.5: 9: 1 v/v] 0.56. $^1$H NMR (400 MHz, $CDCl_3$) δH (ppm) 5.50 (1H, s, br, amide NH), 3.99 (2H, s, br, $NHCH_2$), 3.35-3.25 (2H, d, br, $OCNCH_2$), 3.17-3.07 (2H, d, br, $OCNCH_2$), 1.44 (9H, s, $C(CH_3)3$), 1.61-1.44 (13H, m,

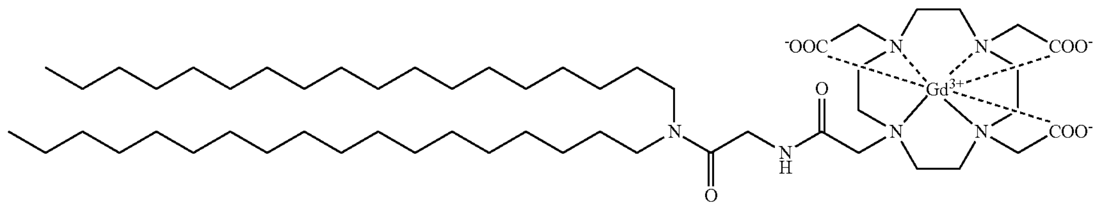

A stoichiometric amount of $GdCl_3.6H_2O$ (28.118 mg, 0.075 mmol) was added to DOTA.DSA (3) (73 mg, 0.0757 mmol), and the reaction was stirred in distilled $H_2O$ (20 mL) at 90° C. overnight (pH dropped to 3.5 upon gadolinium addition). The water was freeze-dried to yield a white powder (83.9 mg, 99% yield, decomp.=345-348° C.). Rf [$CH_2Cl_2$: MeOH: $H_2O$: 34.5: 9: 1 v/v] 0.55. The xylenol orange test indicated no detectable free $Gd^{3+}$ ions. FTIR: vmax (nujol)/$cm^{-1}$ 3750.23, 2234.78, 1991.59, 1889.89, 1793.44, 1681.90.77. HPLC: tR=36.22 min, column C-4 peptide, gradient mix: 0.0 min [100% A], 15-25.0 min [100% B], 25.1-45.0 min [100% C], 45.1-55.0 min [100% A]; flow: 1 mL/min. MS (ESI+) calculated for C54H101GdN608 m/z 1119.67, found 1120.10 $(M+H)^+$.

(iii) N, N-Distearylamidomethylcarbamic Acid Tert-Butyl Ester (2a)

$C(CH_3)_3$ and $OCN(CH_2CH_2)$), 1.25 (60H, s, $CH_2$'s alkyl chain), 0.872 (6H, s, br, $CH_3$×2). ‾C NMR (400 MHz, $CDCl_3$) δC (ppm) 167.6 ($CON(CH_2)17$), 156.0 ($C(CH_3)_3$ COCO), 79.0 ($C(CH_3)_3$), 46.0 ($N(CH_2CH_2)9$), 46.1 ($N(CH_2CH_2)9$), 42.2 ($NHCH_2CO$), 31.9-26.9 ($CH_2$×30), 22.7 ($N(CH_2CH_2)9$), 14.1 (C(CH3)3). FTIR: vmax (nujol)/$cm^{-1}$ 2360.56, 1723.85, 1650.78, 1580.63, 1377.25. HPLC: tR=36.08 min, column C-4 peptide, gradient mix: 0.0 min [100% A], 15-25.0 min [100% B], 25.1-45.0 min [100% C], 45.1-55.0 min [100% A]; flow: 1 mL/min. HRMS (FAB+) calculated for C43H86N203 m/z 678.6638, found 679.6953 $(M+H)^+$.

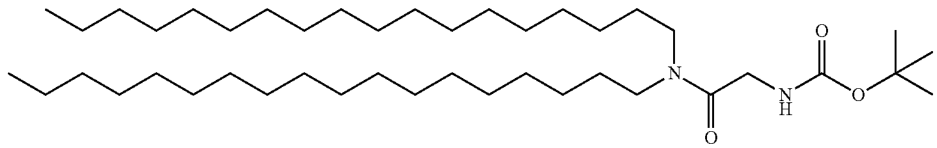 [SMILES: CCCCCCCCCCCCCCCCCCN(CCCCCCCCCCCCCCCCCC)C(=O)CNC(=O)OC(C)(C)C]

(iv) N,N-Distearylamidomethylamine (DSA) (2)

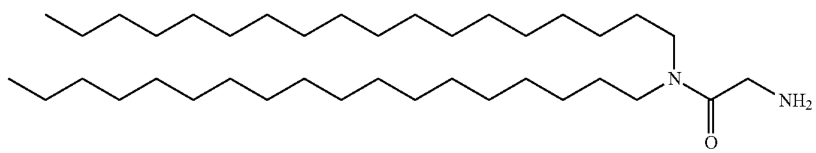 [SMILES: CCCCCCCCCCCCCCCCCCN(CCCCCCCCCCCCCCCCCC)C(=O)CN]

The protected amine 2a was dissolved in anhydrous $CH_2Cl_2$ (5 mL), to which was added trifluoroacetic acid (3 mL). The reaction was stirred under an atmosphere of $N_2$ for 2 h. The solvents were removed in vacuo and the product dried under vacuum to obtain a white powder (158 mg, 94% yield, mp=59-64° C.). Rf [Hexane: Ethyl acetate: 9:1 v/v] 0.44. $^1$H NMR (400 MHz, CDCl3) δH (ppm) 3.85 (2H, s, $OCCH_2NH_2$), 3.32 (2H, t, J 7.2 Hz, $OCNCH_2CH_2$), 3.13 (2H, t, J 7.2 Hz, $OCNCH_2CH_2$), 2.39 (2H, s, very br, $NH_2$), 1.61-1.55 (4H, m, $OCNCH_2CH_2$), 1.26 (60H, s, chain $CH_2$'s), 0.86 (6H, t, J 6.8, $CH_3$×2). $^{13}$C NMR (400 MHz, CDCl3) δC (ppm) 168.8 (CO), 43.7 (OCN $CH_2$), 41.9 ($OCNCH_2$), 35.6 ($CH_3CH_2CH_2$), 33.4 (alkyl chain $CH_2$'s), 32.3, 31.1 ($NCH_2CH_2CH_2$), 22.7-14.1 (alkyl chain $CH_2$'s). FTIR: vmax (nujol)/$cm^{-1}$ 1681, 1534, 1313, 1206, 1174. HPLC: R=31.46 min, column C-4 peptide, gradient mix: 0.0 min [100% A], 15-25.0 min [100% B], 25.1-45.0 min [100% C], 45.1-55.0 min [100% A]; flow: 1 mL/min. HRMS (FAB+) calculated for C38H78N2O m/z 578.6114, found 579.6199 $(M+H)^+$.

Figure 1:
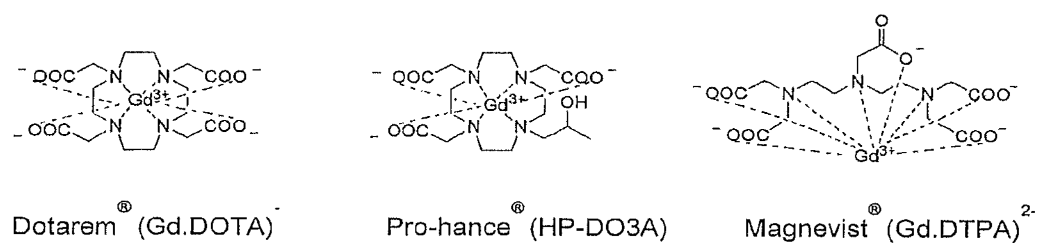
FIG. 1 shows Gadolinium based clinical contrast agents approved by the FDA.
Figure 2:
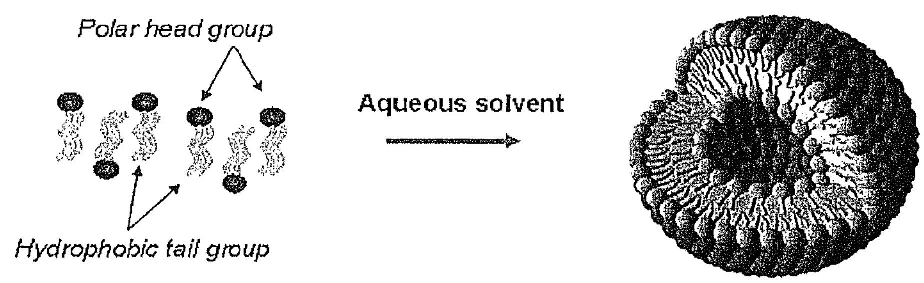
FIG. 2 shows liposome formation from amphipathic lipids.
Figure 3:
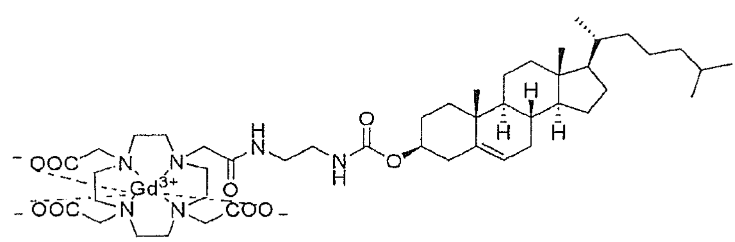
FIG. 3 shows Gd.DOTA.Chol, a $T_1$ lipidic contrast agent component of MAGfect.
Figure 4:
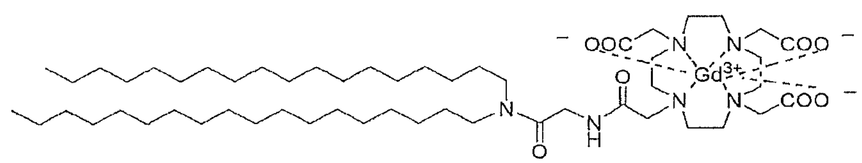
FIG. 4 shows the paramagnetic gadolinium lipid target, Gd.DOTA.DSA.
Figure 5:
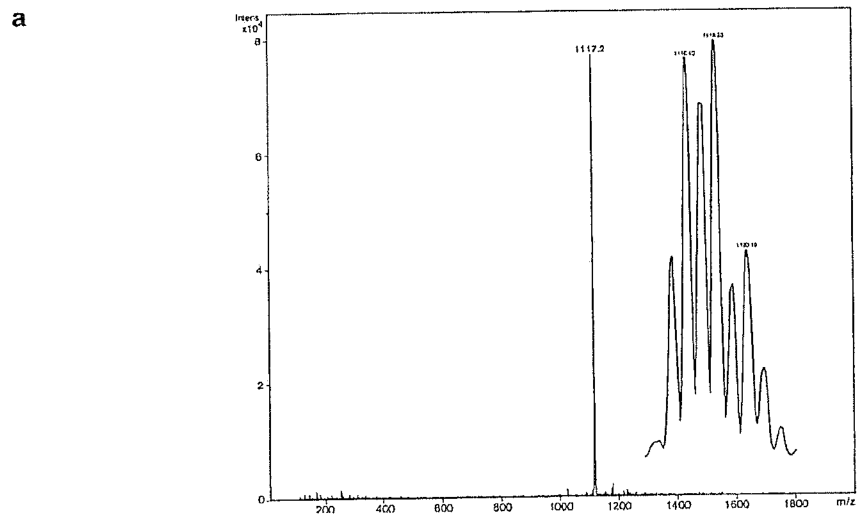
FIG. 5 shows an electrospray mass spectrum of Gd.DOTA.DSA, m/z: 1117.2 (M−H), the isotopic peaks of Gd are visible in the top right corner.
Figure 6:
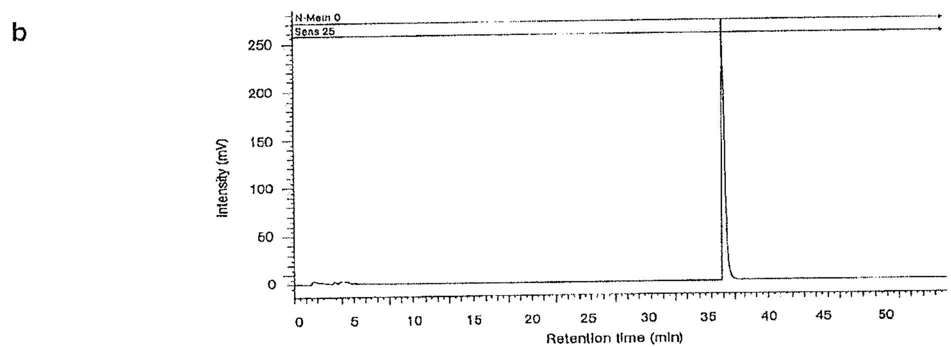
FIG. 6 shows an HPLC trace of Gd.DOTA.DSA 2: $t_R$=36.22 min, column C-4 peptide; gradient mix A=MeCN/0.1% TFA; mix B=$H_2O$/TFA; mix C=MeOH, 0.0 min [100% B], 15-25.0 min [100% A], 25.1-45.0 min [100% C]; flow 1 mL/min.

Due to the paramagnetic nature of lipid 4, NMR spectroscopy was not suitable as a characterisation tool due to the extreme peak broadening caused by the paramagnetic gadolinium metal. All gadolinium lipids were analysed by electrospray mass spectrometry (ESI-MS), HPLC and the xylenol orange assay was used to test for the presence of any free $Gd^{3+}$ in the product samples. The xylenol orange assay is a colourimetric test whereby a colour change from orange to purple is indicative of $Gd^{3+}$ complexation to the xylenol orange dye. This causes a bathochromic shift from 440 nm to 573 nm. Here, by using a standard calibration curve of known gadolinium concentrations versus absorbance, the amount of free $Gd^{3+}$ in the sample could therefore be assessed. As presented in FIGS. 5 and 6 HPLC and MS analysis of Gd.DOTA.DSA 4 was carried out and no free $Gd^{3+}$ was shown to be present, and the compound was prepared with 98% purity and excellent yields. The isotopic peaks of gadolinium were also visible in the MS trace and as a result the observation of the abundant isotopes of gadolinium confirmed complexation of the metal with the DOTA lipid. The HPLC, MS and the isotopic gadolinium peaks for compound 4 are shown in FIGS. 5 and 6.

Xylenol Orange Test

The presence of free gadolinium ions in Gd incorporated compounds was determined by measuring the absorbance at 573 nm of a mixture of xylenol orange solution (990 μL, 0.5 mM in sodium acetate buffer (0.1 M, pH 5.2) and test solution (in 1:1 MeOH: $CH_2Cl_2$) containing the Gd compound (10 μL). Extinction coefficient ε=20, 700 L $mol^{-1}$ $cm^{-1}$ whereby [Free Gd]=A573/ε.

MRI Analysis of Gd.DOTA.DSA For $T_1$ analysis, Gd.DOTA.DSA 4, Gd.DTPA.BSA, and controls of the metal free compound, and Magnevist (Schering A G, Germany) were added to water to give a final concentration of 0.5 mM. The solutions (200 μL) were placed in eppendorf tubes and $T_1$ relaxation values measured on a 4.7 T Varian MR scanner at ambient temperature. For relaxivity measurements; gadolinium liposome formulations were prepared in order to obtain five different gadolinium concentrations between 0.20 to 0.66 M in 200 μL of distilled water and the molar relaxivity $r_1$ ($mM^{-1}$ $s^{-1}$) determined. $T_1$ values were obtained using saturation recovery experiments performed with a standard spin-echo sequence and a 2 mm single slice acquisition (TR=50, 100, 200, 300, 500, 700, 1200, 3000, 5000, 7000 ms, TE=15 ms), number of signal averages; 2, FOV; 70×70 $mm^2$, collected into a matrix of 256×128.

Liposome Preparations All lipids were stored as stock solutions in anhydrous organic solvents ($CHCl_3$, MeOH or a mixture of both), at −20° C. under argon. Appropriate volumes of each lipid stock were placed in a round bottom flask containing chloroform and stirred to ensure thorough mixing of the lipids. The solvent was slowly removed in vacuo to ensure production of an even lipid film. The film was re-hydrated with buffer (HEPES, NaCl, 150 mM, pH 6.8) at a defined volume (20 mL per 500 mg liposome). The resulting solution was sonicated for 60 min (at 30° C.). The pH of the liposomal suspension was checked by pH Boy (Camlab Ltd., Over, Cambridgeshire, UK). For each preparation, the size and polydispersity of liposomes was measured by photon correlation spectroscopy (PCS).

Mouse Tumour Model IGROV-1 cells ($5\times10^6$/0.1 mL PBS) were implanted into the flanks of 6-8 weeks old Balb/c nude mice for generation of subcutaneous tumours. After ~2 weeks (estimated tumour weights 40-50 mg) the mice were anaesthetized with an isoflurane/$O_2$ mix and placed into a quadrature $^1$H volume coil and positioned into the magnet. Baseline scans were obtained and then the mice were injected intravenously via lateral tail vein with either a 200 μL liposome solution (HEPES (20 mM, NaCl 135 mM, pH 6.5)) and imaged at 4.7 T (spin echo sequence: TR=400-2800 ms, TE=10 ms, FOV=45×45 $cm^2$, averages: 1, matrix size: 256×128 thickness: 2.0 mm, and 20 slices).

Histology Experiments Following MRI, the animals were sacrificed and the tumours, livers and kidneys were excised, frozen in liquid nitrogen, embedded in OCT (VWR) embedding fluid and either 10 or 7 m thick sections cut, mounted on slides and studied for fluorescence microscopy.

REFERENCES

[1] Shah, K.; Jacobs, A.; Breakefield, X. O.; Weissleder, R. Molecular imaging of gene therapy for cancer. *Gene Therapy* 2004, 11, 1175-1187.

[2] Massoud, T. F.; Gambhir, S. S. Molecular imaging in living subjects: seeing fundamental biological processes in a new light. *Genes & Development* 2003, 17, 545-580.

[3] Caravan, P.; Ellison, J. J.; McMurry, T. J.; Lauffer, R. B. Gadolinium(III) chelates as MRI contrast agents: Structure, dynamics, and applications. *Chemical Reviews* 1999, 99, 2293-2352.

[4] Parac-Vogt, T. N.; Kimpe, K.; Laurent, S.; Pierart, C.; Elst, L. V.; Muller, R. N.; Binnemans, K. *European Journal of Inorganic Chemistry* 2004, 3538-3543

[5] Tilcock, C., Unger, E., Cullis, P. and MacDougall, P. *Radiology* 1989, 17

6 Oliver, M.; Ahmad, A.; Kamaly, N.; Perouzel, E.; Caussin, A.; Keller, M.; Herlihy, A.; Bell, J.; Miller, A. D.; Jorgensen, M. R. *Organic and Biomolecular Chemistry* 2006, 4, 3489-3497

[7] Kabalka, G. W., Davis, M. A., Holmberg, E., Maruyama, K. and Huang, L. *Magnetic Resonance Imaging* 1991, 9, 373377

[8] E. C Unger, T. A. F., C. Tilcock, T. E. *New Journal of Magnetic Resonance Imaging* 1991, 6, 689-693

[9] Bhattacharya, S.; Haldar, S. *Biochimica Et Biophysica Acta* 2000, 1467, 39-53

[10] Lian, T.; Ho, R. J. Y. *Journal of Pharmaceutical Sciences* 2001, 90, 667-680.

[11] Moghimi, S. M.; Szebeni, J. *Progress in Lipid Research* 2003, 42, 463-478.

[12] Scherphof, G. L.; Velinova, M.; Kamps, J.; Donga, J. In *Liposome research days: Towards new products for human health*; Hirota, S., Ed.; Elsevier: Shizuoka; Japan, 1996, p 179-192.

[13] Maeda, H.; Wu, J.; Sawa, T.; Matsumura, Y.; Hori, K. In *Recent advances in drug delivery systems*; Anderson, J. M., Kim, S. W., Kopecek, J., Robinson, J. R., Eds.; Elsevier: Salt Lake City, Utah, 1999, p 271-284

[14] Iyer, A. K.; Khaled, G.; Fang, J.; Maeda, H. /*Drug Discovery Today* 2006, 11, 812-818

[15] Ke, C. Y., Mathias, C. J., and Green, M. A. (2004) Folate-receptor-targeted radionuclide imaging agents. *Adv. Drug Delivery Rev.* 56, 1143-1160. Reddy, J. A., Allagadda, V. M., and Leamon, C. P. (2005) Targeting Therapeutic and Imaging Agents to Folate Receptor Positive Tumours. *Curr. Pharm. Biotechnol* 6, 131-150. Wang, Z. J., Boddington, S., Wendland, M., Meier, R., Corot, C., and Daldrup-Link, H. (2008) MR imaging of ovarian tumours using folate-receptor-targeted contrast agents. *Pediatric Radiol.* 38, 529-537. Saul, J. M., Annapragada, A. V., and Bellamkonda, R. V. (2006) A dual-ligand approach for enhancing targeting selectivity of therapeutic nanocarriers. *J. Controlled Release* 114, 277287. Ghaghada, K. B., Saul, J., Natarajan, J. V., Bellamkonda, R. V., and Annapragada, A. V. (2005) Folate targeting of drug carriers: A mathematical model. *J. Controlled Release* 104, 113-128. Müller, C., Schubiger, P. A., and Schibli, R. (2006) In vitro and in vivo targeting of different folate receptor-positive cancer cell lines with a novel 99mTc-radiofolate tracer. *Eur. J. Nucl. Med. Mol. Imaging* 33, 1162-1170. Hilgenbrink, A. R., and Low, P. S. (2005) Folate Receptor-Mediated Drug Targeting: From Therapeutics to Diagnostics. *J. Pharm. Sci.* 94, 2135-2146. Henriksen, G., Bruland, 0. S., and Larsen, R. H. (2005) Preparation and Preclinical Assessment of Folate-conjugated, Radiolabelled Antibodies. *Anticancer Res.* 25, 9-16. Wang, S., Luo, J., Lantrip, D. A., Waters, D. J.; Mathias, C. J., Green, M. A., Fuchs, P. L. and Low, P. S. (1997) Design and Synthesis of [111In]DTPA-Folate for Use as a Tumour-Targeted Radiopharmaceutical. *Bioconjugate Chem.* 8, 673-679. Sudimack, J., and Lee, R. J. (2000) Targeted drug delivery via the folate receptor. *Adv. Drug Delivery Rev.* 41, 147-162. Hofland, H. E., Masson, C., Iginla, S., Osetinsky, I., Reddy, J. A., Leamon, C. P., Scherman, D., Bessodes, M., and Wils, P. (2002) Folate-Targeted Gene Transfer in Vivo. *Molecular Therapy* 5, 739744.

16 Gabizon, A., Horowitz, A. T., Goren, D., Tzemach, D., Shmeeda, H., and Zalipsky, S. (2003) In Vivo Fate of Folate-Targeted Polyethylene-Glycol Liposomes in Tumour-Bearing Mice. *Clin. Cancer Res.* 9, 6551-6559. Salazar, M. D., and Ratnam, M. (2007) The folate receptor: What does it promise in tissue-targeted therapeutics? *Cancer Metastasis Rev.* 26, 141-152.

[17] Low, P. S., Henne, W. A., and Doorneweerd, D. D. (2008) Discovery and Development of Folic-Acid-Based Receptor Targeting for Imaging and Therapy of Cancer and Inflammatory Diseases. *Acc. Chem. Res.* 41, 120-129.

[18] Gupta, Y., Jain, A., Jain, P., and Jain, S. (2007) Design and development of folate appended liposomes for enhanced delivery of 5-FU to tumour cells. *J. Drug Targeting* 15, 231-240.

[19] Sega, E. I. and Low, P. S. (2008) Tumour detection using folate receptor-targeted imaging agents. *Cancer and Metastasis Rev.* 27, 655-664.

[20] Kim, I. B., Shin, H., Garcia, A. J., and Bunz, U. H. F. (2007) Use of a Folate-PPE Conjugate To Image Cancer Cells in Vitro. *Bioconjugate Chem.* 18, 815-820.

[21] Konda, S. D., Aref, M., Wang, S., Brechbiel, M., and Wiener, E. C. (2001) Specific targeting of folate-dendrimer MRI contrast agents to the high affinity folate receptor expressed in ovarian tumour xenografts. *Magma* 12, 104 -113.

[22] Oyewumi, M. O., Yokel, R. A., Jay, M., Coakley, T., and Mumper, R. J. (2004) Comparison of cell uptake, biodistribution and tumour retention of folate-coated and PEG-coated gadolinium nanoparticles in tumour-bearing mice. *J. Controlled Release* 95, 613-626.

[23] Choi, H., Choi, S. R., Zhou, R., Kung, H. F., and Chen, I. W. (2004) Iron oxide nanoparticles as magnetic resonance contrast agent for tumour imaging via folate receptor-targeted delivery. *Acad. Radiol.* 11, 996-1004.

[24] Kamaly, N., Kalber, T., Ahmad, A., Oliver, M. H., So, P. W., Herlihy, A. H., Bell, J. D., Jorgensen, M. R., and Miller, A. D. (2008) Bimodal Paramagnetic and Fluorescent Liposomes for Cellular and Tumour Magnetic Resonance Imaging. *Bioconjugate Chem.* 19, 118-129.

[25] Torchilin, V. P. (2007) Targeted Pharmaceutical Nanocarriers for Cancer Therapy and Imaging. *The AAPS Journal* 9, E128-E147.

[26] Sun, C., Sze, R., and Zhang, M. (2006) Folic acid-PEG conjugated superparamagnetic nanoparticles for targeted cellular uptake and detection by MRI. *J. Biomed. Mater. Res. Part A* 78, 550-557.

[27] Muller, C., Schubiger, P. A., and Schibli, R. (2006) In vitro and in vivo targeting of different folate receptor-positive cancer cell lines with a novel 99mTc-radiofolate tracer. *Eur. J. Nucl. Med. Mol. Imaging* 33, 1162-1170.

[28] Wu, J., Liu, Q., and Lee, R. J. (2006) A folate receptor-targeted liposomal formulation for paclitaxel. *Int. J. Pharm.* 316, 148-153.

[29] Wu, M., Gunning, W., and Ratnam, M. (1999) Expression of Folate Receptor Type ain Relation to Cell Type, Malignancy, and Differentiation in Ovary, Uterus, and Cervix. *Cancer Epidemiology Biomarkers and Prevention* 8, 775782.

[30] Stevens, P. J., Sekido, M., and Lee, R. J. A (2004) Folate Receptor-Targeted Lipid Nanoparticle Formulation for a Lipophilic Paclitaxel Prodrug. *Pharm, Res.* 21, 2153-2157.

[31] Gabizon, A. A., Shmeeda, H., and Zalipsky, S. (2005) Pros and Cons of the Liposome Platform in Cancer Drug Targeting. International Liposome Society (ILS 2005). *Liposome advances: progress in drug and vaccine delivery, pp* 175-184, Taylor & Francis, London.

The invention claimed is:

1. A liposome comprising Gd.DOTA.DSA (gadolinium (III) 2-{4,7-bis-carboxymethyl-10-[(N,N-distearylamidomethyl-N'-amido-methyl]-1,4,7,10-tetra-azacyclododec-1-yl}-acetic acid), wherein the amount of Gd.DOTA.DSA in said liposome is from 29 to 31 mol % of the total liposome formulation, a neutral, fully saturated phospholipid component, wherein said neutral, fully saturated phospholipid component is a 1,2-di($C_{12}$-$C_{20}$ saturated lipid)-sn-glycero-3-phosphocholine, wherein the saturated lipid groups can be the same or different from each other, wherein the amount of neutral, fully saturated phospholipid component in said liposome is from 32 to 34 mol % of the total liposome formulation;

a polyethylene glycol-phospholipid component, wherein the amount of the polyethylene glycol-phospholipid component is from 6 to 7 mol % of the total liposome formulation; wherein (a) average size of the liposomes is at or less than 100 nm;

(b) the liposomes are of low size polydispersity; and (a) and (b) in combination provide for gradual accumulation within tumor tissue, image enhancement and reduced toxicity.

2. A liposome according to claim 1, wherein said neutral, fully saturated phospholipid component is DSPC (1,2-distearoyl-sn-glycero-3-phosphocholine).

3. A liposome according to claim 1, wherein said liposome further comprises cholesterol.

4. A liposome according to claim 3, wherein the amount of cholesterol in said liposome is from 29 to 31 mol % of the total liposome formulation.

5. A liposome according to claim 1, wherein said polyethylene glycol-phospholipid component is DSPE-PEG (2000) [distearoylphosphatidylethanolamine-polyethylene glycol (2000)].

6. A liposome according to claim 1, wherein said liposome has an average particle size of less than or equal to 80 nm.

7. A liposome according to claim 1, wherein said liposome comprises Gd.DOTA.DSA, cholesterol, DSPC and DSPE-PEG(2000).

8. A liposome according to claim 1, wherein said liposome further comprises a tumor targeting agent.

9. A liposome according to claim 8, wherein said tumor targeting agent comprises a ligand for a receptor that is over-expressed in tumor cells relative to the expression of said receptors in the cells of non-tumorous tissue of mammals.

10. A liposome according to claim 9, wherein said tumor targeting agent comprises a folate moiety.

11. A liposome according to claim 10, wherein the amount of said folate moiety present in said liposome is 1-2 mol % of the total liposome formulation.

12. A liposome according to claim 9, wherein said tumor targeting agent is a phospholipid-polyethylene glycol-folate compound.

13. A liposome according to claim 12, wherein said phospholipid-polyethylene glycol-folate compound is DSPE-PEG(2000)-Folate [distearoylphosphatidylethanolamine-polyethylene glycol (2000)-folate].

14. A liposome according to claim 8, wherein said liposome comprises Gd.DOTA.DSA, cholesterol, DSPC, DSPE-PEG(2000) and DSPE-PEG(2000)-Folate.

15. A magnetic resonance contrast agent, comprising a liposome according to claim 1 and a pharmaceutically acceptable carrier.

16. A magnetic resonance contrast agent according to claim 15, wherein said pharmaceutically acceptable carrier is an aqueous carrier.

17. A method of magnetic resonance imaging of an organ or organ structure in a mammal, comprising the steps of: (a) administering the magnetic resonance contrast agent according to claim 15 to the mammal; and (b) taking images of the organ or organ structure in the mammal.

18. A method according to claim 17, wherein said magnetic resonance contrast agent enhances a magnetic resonance image of a tumor in the mammal.

19. A method according to claim 17, wherein the concentration of the liposome in said magnetic resonance contrast agent is 1-50 mg/mL.

20. A method of magnetic resonance imaging of an organ or organ structure in a mammal pre-administered with the magnetic contrast agent according to claim 15 comprising the step of: (i) taking images of the organ or organ structure in the mammal.

21. A method of making a magnetic contrast agent according to claim 15 comprising mixing said liposome and said pharmaceutically acceptable carrier.

* * * * *